(12) United States Patent
Luo et al.

(10) Patent No.: US 10,869,910 B2
(45) Date of Patent: *Dec. 22, 2020

(54) MOLECULAR DESIGN OF RECOMBINANT PROTEIN DRUG

(71) Applicants: Tsinghua University, Beijing (CN); BEIJING PROTGEN LTD., Beijing (CN)

(72) Inventors: Yongzhang Luo, Beijing (CN); Peng Liu, Beijing (CN); Xinan Lu, Beijing (CN)

(73) Assignees: Tsinghua University, Beijing (CN); BEIJING PROTGEN LTD., Beijing (CN)

( * ) Notice: Subject to any disclaimer, the term of this patent is extended or adjusted under 35 U.S.C. 154(b) by 210 days.

This patent is subject to a terminal disclaimer.

(21) Appl. No.: 15/550,751

(22) PCT Filed: Feb. 14, 2016

(86) PCT No.: PCT/CN2016/073773
§ 371 (c)(1),
(2) Date: Dec. 22, 2017

(87) PCT Pub. No.: WO2016/127948
PCT Pub. Date: Aug. 18, 2016

(65) Prior Publication Data
US 2018/0200337 A1  Jul. 19, 2018

(30) Foreign Application Priority Data

Feb. 13, 2015 (CN) .......................... 2015 1 0079486
Nov. 2, 2015 (CN) .......................... 2015 1 0736184

(51) Int. Cl.
| | | |
|---|---|---|
| A61K 38/18 | (2006.01) |
| A61K 38/17 | (2006.01) |
| C07K 14/435 | (2006.01) |
| C07K 14/78 | (2006.01) |
| A61K 47/50 | (2017.01) |
| A61P 5/50 | (2006.01) |
| A61P 35/00 | (2006.01) |
| A61K 47/10 | (2017.01) |

(52) U.S. Cl.
CPC .......... *A61K 38/1891* (2013.01); *A61K 38/17* (2013.01); *A61K 47/10* (2013.01); *A61K 47/50* (2017.08); *A61P 5/50* (2018.01); *A61P 35/00* (2018.01); *C07K 14/435* (2013.01); *C07K 14/78* (2013.01)

(58) Field of Classification Search
None
See application file for complete search history.

(56) References Cited

U.S. PATENT DOCUMENTS

| | | |
|---|---|---|
| 2014/0308263 A1 | 10/2014 | Luo et al. |
| 2015/0197733 A9 | 7/2015 | Luo et al. |
| 2018/0015148 A1* | 1/2018 | Luo ........................ A61K 38/39 |

FOREIGN PATENT DOCUMENTS

| | | | |
|---|---|---|---|
| EP | 2754718 B1 | 12/2017 |
| WO | WO2013-034116 | * | 3/2013 |
| WO | WO 2013034116 A1 | 3/2013 |

OTHER PUBLICATIONS

International Search Report for PCT/CN2016/073773, dated May 18, 2016, 6 pages.
Written Opinion of the International Search Authority for PCT/CN2016/073773, dated May 18, 2016, 6 pages.

* cited by examiner

*Primary Examiner* — James H Alstrum-Acevedo
*Assistant Examiner* — Tara L Martinez
(74) *Attorney, Agent, or Firm* — Morrison & Foerster LLP

(57) ABSTRACT

Provided is a mutant of an endostatin. The mutant has improved ATPase activity and improved activity of inhibiting angiogenesis and inhibiting tumors. Further provided is use of the mutant in treatment of angiogenesis related diseases such as tumors.

7 Claims, 16 Drawing Sheets
Specification includes a Sequence Listing.

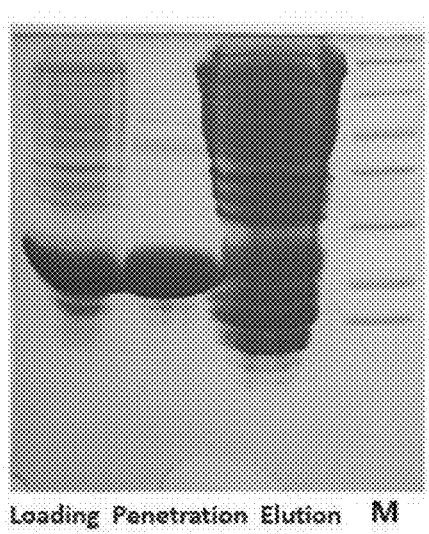
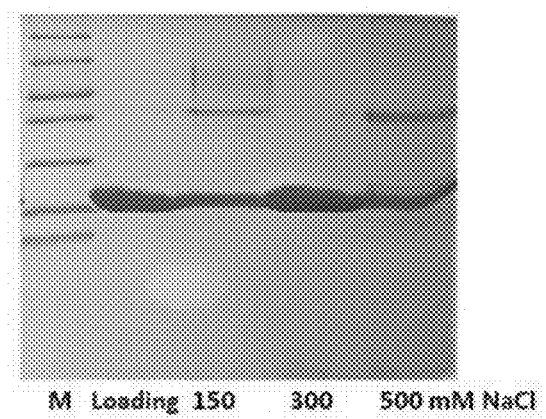
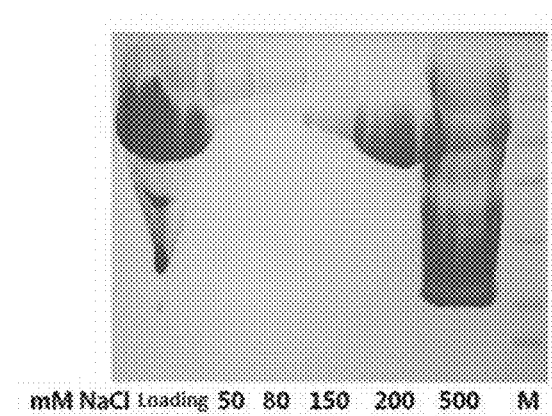
Figure 2

(M)HSHRDFQPVLHLVALNSPLSGGMR
GIRGADFQCFQQARAVGLAGTFRAFLS
SRLQDLYSIVRRADRAAVPIVNLKDELL
FPSWEALFSGSEGPLKPGARIFSFDGKD
VLRHPTWPQKSVWHGSDPNGRRLTES
YCETWRTEAPSATGQASSLLGGRLLGQ
SAASCHHAYIVLCIENSFMTASK

Figure 3

(M)DFQPVLHLVALNSPLSGGMRGIRGA
DFQCFQQARAVGLAGTFRAFLSSRLQD
LYSIVRRADRAAVPIVNLKDELLFPSWE
ALFSGESGAGKTPGARIFSFDGKDVLRH
PTWPQKSVWHGSDPNGRRLTESYCET
WRTEAPSATGQASSLLGGRLLGQSAAS
CHHAYIVLCIENSFMTASK

Figure 4

(M)DFQPVLHLVALNSPLSGGMRGIRGA
DFQCFQQARAVGLAGTFRAFLSSRLQD
LYSIVRRADRAAVPIVNLKDELLFPSWE
ALFSGSEGPLKSPGARIFSFDGKDVLRH
PTWPQKSVWHGSDPNGRRLTESYCET
WRTEAPSATGQASSLLGGRLLGQSAAS
CHHAYIVLCI

Figure 5

(M)DFQPVLHLVALNSPLSGGMRGIRGA
DFQCFQQARAVGLAGTFRAFLSSRLQD
LYSIVRRADRAAVPIVNLKDELLFPSWE
ALFSGSEGPLKTPGARIFSFDGKDVLRH
PTWPQKSVWHGSDPNGRRLTESYCET
WRTEAPSATGQASSLLGGRLLGQSAAS
CHHAYIVLCI

Figure 6

(M)DFQPVLHLVALNSPLSGGMRGIRGA
DFQCFQQARAVGLAGTFRAFLSSRLQD
LYSIVRRADRAAVPIVNLKDELLFPSWE
ALFSGESGAGKTPGARIFSFDGKDVLRH
PTWPQKSVWHGSDPNGRRLTESYCET
WRTEAPSATGQASSLLGGRLLGQSAAS
CHHAYIVLCI

Figure 7

(M)HSHRDFQPVLHLVALNSPLSGGMR
GIRGADFQCFQQARAVGLAGTFRAFLS
SRLQDLYSIVRRADRAAVPIVNLKDELL
FPSWEALFSGESGAGKTPGARIFSFDGK
DVLRHPTWPQKSVWHGSDPNGRRLTE
SYCETWRTEAPSATGQASSLLGGRLLG
QSAASCHHAYIVLCIEN

Figure 8

(M)HSHRDFQPVLHLVALNSPLSGGMR
GIRGADFQCFQQARAVGLAGTFRAFLS
SRLQDLYSIVRRADRAAVPIVNLKDELL
FPSWEALFSGESGAGKTPGARIFSFDGK
DVLRHPTWPQKSVWHGSDPNGRRLTE
SYCETWRTEAPSATGQASSLLGGRLLG
QSAASCHHAYIVLCIENSFM

Figure 9

(M)HSHRDFQPVLHLVALNSPLSGGMR
GIRGADFQCFQQARAVGLAGTFRAFLS
SRLQDLYSIVRRADRAAVPIVNLKDELL
FPSWEALFSGSEGPLKPGARIFSFDGKD
VLRHPTWPQKSVWHGSDPNGRRLTES
YCETWRTEAPSATGQASSLLGGRLLGQ
SAASCHHAYIVLCIEN

Figure 10

(M)HRDFQPVLHLVALNSPLSGGMRGIR
GADFQCFQQARAVGLAGTFRAFLSSRL
QDLYSIVRRADRAAVPIVNLKDELLFPS
WEALFSGESGAGKTPGARIFSFDGKDV
LRHPTWPQKSVWHGSDPNGRRLTESY
CETWRTEAPSATGQASSLLGGRLLGQS
AASCHHAYIVLCIEN

Figure 11

(M)HRDFQPVLHLVALNSPLSGGMRGIR
GADFQCFQQARAVGLAGTFRAFLSSRL
QDLYSIVRRADRAAVPIVNLKDELLFPS
WEALFSGESGAGKTPGARIFSFDGKDV
LRHPTWPQKSVWHGSDPNGRRLTESY
CETWRTEAPSATGQASSLLGGRLLGQS
AASCHHAYIVLCIENSFM

Figure 12

(M)HRDFQPVLHLVALNSPLSGGMRGIR
GADFQCFQQARAVGLAGTFRAFLSSRL
QDLYSIVRRADRAAVPIVNLKDELLFPS
WEALFSGESGAGKTPGARIFSFDGKDV
LRHPTWPQKSVWHGSDPNGRRLTESY
CETWRTEAPSATGQASSLLGGRLLGQS
AASCHHAYIVLCIENSFMTAS

Figure 13

(M)SHRDFQPVLHLVALNSPLSGGMRGI
RGADFQCFQQARAVGLAGTFRAFLSSR
LQDLYSIVRRADRAAVPIVNLKDELLFP
SWEALFSGESGAGKTPGARIFSFDGKD
VLRHPTWPQKSVWHGSDPNGRRLTES
YCETWRTEAPSATGQASSLLGGRLLGQ
SAASCHHAYIVLCIENSFMTAS

Figure 14

(M)SHRDFQPVLHLVALNSPLSGGMRGI
RGADFQCFQQARAVGLAGTFRAFLSSR
LQDLYSIVRRADRAAVPIVNLKDELLFP
SWEALFSGESGAGKTPGARIFSFDGKD
VLRHPTWPQKSVWHGSDPNGRRLTES
YCETWRTEAPSATGQASSLLGGRLLGQ
SAASCHHAYIVLCIEN

Figure 15

(M)SHRDFQPVLHLVALNSPLSGGMRGI
RGADFQCFQQARAVGLAGTFRAFLSSR
LQDLYSIVRRADRAAVPIVNLKDELLFP
SWEALFSGESGAGKTPGARIFSFDGKD
VLRHPTWPQKSVWHGSDPNGRRLTES
YCETWRTEAPSATGQASSLLGGRLLGQ
SAASCHHAYIVLCIENSFM

Figure 16

(M)SHRDFQPVLHLVALNSPLSGGMRGI
RGADFQCFQQARAVGLAGTFRAFLSSR
LQDLYSIVRRADRAAVPIVNLKDELLFP
SWEALFSGESGAGKTPGARIFSFDGKD
VLRHPTWPQKSVWHGSDPNGRRLTES
YCETWRTEAPSATGQASSLLGGRLLGQ
SAASCHHAYIVLCIENSFMTASK

Figure 17

(M)HRDFQPVLHLVALNSPLSGGMRGIR
GADFQCFQQARAVGLAGTFRAFLSSRL
QDLYSIVRRADRAAVPIVNLKDELLFPS
WEALFSGESGAGKTPGARIFSFDGKDV
LRHPTWPQKSVWHGSDPNGRRLTESY
CETWRTEAPSATGQASSLLGGRLLGQS
AASCHHAYIVLCIENSFMTASK

Figure 18

(M)HSHRDFQPVLHLVALNSPLSGGMR
GIRGADFQCFQQARAVGLAGTFRAFLS
SRLQDLYSIVRRADRAAVPIVNLKDELL
FPSWEALFGESGAGKTPGARIFSFDGK
DVLRHPTWPQKSVWHGSDPNGRRLTE
SYCETWRTEAPSATGQASSLLGGRLLG
QSAASCHHAYIVLCIENSFMTASK

Figure 19

(M)HSHRDFQPVLHLVALNSPLSGGMR
GIRGADFQCFQQARAVGLAGTFRAFLS
SRLQDLYSIVRRADRAAVPIVNLKDELL
FPSWEALFSGESGAGKTPARIFSFDGKD
VLRHPTWPQKSVWHGSDPNGRRLTES
YCETWRTEAPSATGQASSLLGGRLLGQ
SAASCHHAYIVLCIENSFMTASK

Figure 20

```
(M)HSHRDFQPVLHLVALNSPLSGGMR
GIRGADFQCFQQARAVGLAGTFRAFLS
SRLQDLYSIVRRADRAAVPIVNLKDELL
FPSWEALFSGESGAGKTGARIFSFDGK
DVLRHPTWPQKSVWHGSDPNGRRLTE
SYCETWRTEAPSATGQASSLLGGRLLG
QSAASCHHAYIVLCIENSFMTASK
```

Figure 21

```
(M)HSHRDFQPVLHLVALNSPLSGGMR
GIRGADFQCFQQARAVGLAGTFRAFLS
SRLQDLYSIVRRADRAAVPIVNLKDELL
FPSWEALFSGESGAGKTGGARIFSFDG
KDVLRHPTWPQKSVWHGSDPNGRRLT
ESYCETWRTEAPSATGQASSLLGGRLL
GQSAASCHHAYIVLCIENSFMTASK
```

Figure 22

```
(M)HSHRDFQPVLHLVALNSPLSGGMR
GIRGADFQCFQQARAVGLAGTFRAFLS
SRLQDLYSIVRRADRAAVPIVNLKDELL
FPSWEALFSGSEGPLKPGARIFSFDGKD
VLRHPTWPQKSVWHGSDPNGRRLTES
YCETWRTEAPSATGQASSLLGGRLLGQ
SAASCHHAYIVLCIANSFMTASK
```

Figure 23

(M)HSHRDFQPVLHLVALNSPLSGGMR
GIRGADFQCFQQARAVGLAGTFRAFLS
SRLQDLYSIVRRADRAAVPIVNLKDELL
FPSWEALFSGSEGPLKPGARIFSFDGKD
VLRHPTWPQKSVWHGSDPNGRRLTES
YCETWRTEAPSATGQASSLLGGRLLGQ
SAASCHHAYIVLEIENSFMTASK

Figure 24

(M)HSHRDFQPVLHLVALNSPLSGGMR
GIRGADFQCFQQARAVGLAGTFRAFLS
SRLQDLYSIVRRADRAAVPIVNLKDELL
FPSWEALFSGESGAGKTPGARIFSFDGK
DVLRHPTWPQKSVWHGSDPNGRRLTE
SYCETWRTEAPSATGQASSLLGGRLLG
QSAASCHHAYIVLCIENSFMTASK

Figure 25

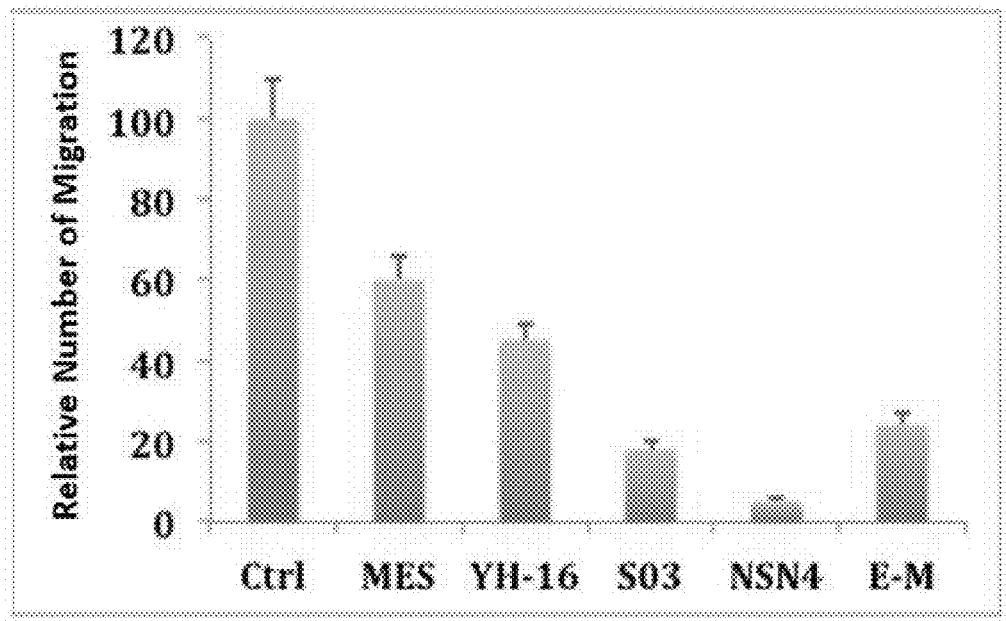

Figure 26

GGAATTCCATATGCACAGCCACCGCGACTTC

CCGCTCGAGTTACTTGGAGGCAGTCATGAAGCTG

36

(M)RDFQPVLHLVALNSPLSGGMRGIRGADFQCFQQARQVGLAGTFRAFLSSRLQDLYSIVRR
ADRAAVPIVNLKDELLFPSWEALFSSEGPLKPGARIFSFDGKDVLRHPTWPQKSVWHGSDPNG
RRLTESYCETWRTEAPSATGQASSLLGGRLLGQSAASCHHAYIVLCIENSFMTASK

249

(M)RDFQPVLHLVALNSPLSGGMRGIRGADFQCFQQARAVGLAGTFRAFLSSRLQDLYSIVRR
ADRGSVPIVNLKDEVLSPSWDSLFSGSQGQLQPGARIFSFDGRDILQDSAWPQKSVWHGSDA
KGRRLPESYCEAWRTDERGTSGQASSLLSGRLLEQKAASCHNSYIVLCIENSFMTASK

381

(M)HVHQDFQPALHLVALNTPLSGGMRGIRGADFQCFQQARQVGLAGTFRAFLSSRLQDLYSI
VRRADRTAVPIVNLRDEVLFSNWEALFTGSEAPLRAGARIFSFDGRDVLRHPTWPQKSVWHG
SDPNGRRLTESYCETWRTEAPSATGQASSLLAGRLLEQKAAGCHNAFIVLCIENSFMTSSSK

57

(M)HTHQDFHPVLHLVALNTPLSGGMRGIRGADFQCFQQARAVGLSGTFRAFLSSRLQDLYSI
VRRADRAAVPIVNLKDELLFPSWEALFSGESGAGKTGGARIFSFDGRDVLRHPAWPQKSVWH
GSDPSGRRLTESYCETWRTDSRAATGQASSLLAGRLLEQKAAGCHNAFIVLCIENSFMTSSSK

114

(M)HSHRDFQPVLHLVALNSPLSGGMRGIRGADFQCFQQARAVGLAGTFRAFLSSRLQDLYSI
VRRADRAAVPIVNLKDELLFPSWEALFSGSEGPLKPGARIFSFDGRDVLRHPTWPQKSVWHGS
DPSGHRLTESYCETWRTDSRAATGQASSLLGGRLLGQSAASCHHAYIVLCIANSFMTASK

124

(M)DFQPVLHLVALNSPLSGGMRGIRGADFQCFQQARAVGLAGTFRAFLSSRLQDLYSIVRRA
DRAAVPIVNLKDELLFPSWEALFSGSEGPLRPGARIFSFDGKDVLRHPTLPQKSVWHGSDPSG
RRLTESYCETWRTDSRAATGQASSLLGGRLLGQSAASCHHAYIVLCIENSFMTASK

125

(M)DFQPVLHLVALNSPLSGGMRGIRGADFQCFQQARAVGLAGTFRAFLSSRLQDLYSIVRRA
DRAAVPIVNLKDELLFPSWEALFSGSEGPLRPGARIFSFDGKDVLRHPTLPQKSVWHGSDPSG
RRLTESYCETWRTDSRAATGQASSLLGGRLLGQSAASCHHAYIVLCIENSFMTASKK

(M)HTHQDFHPVLHLVALNTPLSGGMRGIRGADFQCFQQARAVGLAGTFRAFLSSRLQDLYSI
VRRADRAAVPIVNLKDELLFPSWEALFSGSEGPLKPGARIFSFDGRDILQDSAWPQKSVWHGS
DPNGRRLTESYCETWRTEAPSATGQASSLSSGKLLEQSVSSCQHAFVVLCIENSFMTAAKK

163

(M)TPTWYPRMLRVAALNEPSTGDLQGIRGADFQCFQQARAVGLSGTFRAFLSSRLQDLYSIV
RRADRAAVPIVNLKDEVLSPSWDSLFSGSQGQLQPGARIFSFDGKDVLRHPTWPQKSVWHGS
DPSGRRLMESYCETWRTETTGATGQASSLLGGRLLGQSAASCHHAYIVLCIENSFMTNNRK

119

(M)HTHTSGPGLHLIALNSPQVGNMRGIRGADFQCFQQARAVGLAGTFRAFLSSRLQDLYSIV
RRADRSSVPIVNLKDEVLSPSWDSLFSVSQGQLQPGARIFSFDGRDILQDSAWPQKSVWHGS
DPNGRRLTESYCETWRTEAPSATGQASSLLGGRLLGQSAASCHHAYIVLCIENSFMTASK

Figure 34

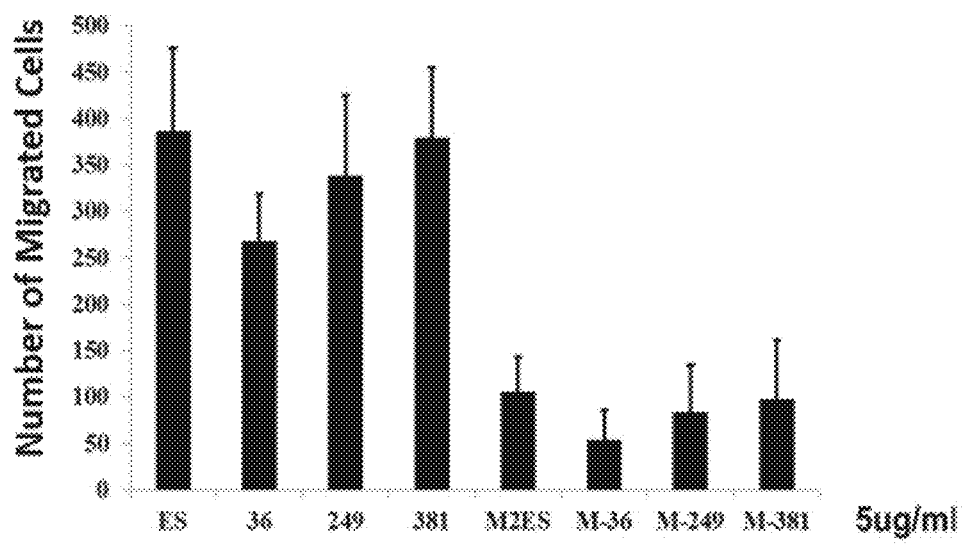

Figure 35

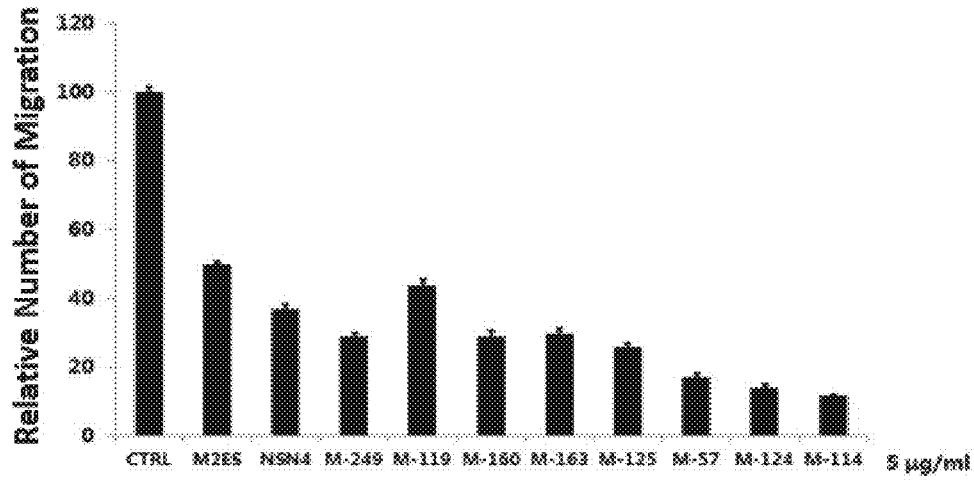

Figure 36

Endu-E-M
MGGSHHHHHHHSHRDFQPVLHLVALNSPLSGGMRGIRGADFQCFQQARAVGLAGTFRAFLSSRLQDLYSIVRR
ADRAAVPIVNLKDELLFPSWEALFSGESGAGKTPGARIFSFDGKDVLRHPTWPQKSVWHGSDPNGRRLTESYC
ETWRTEAPSATGQASSLLGGRLLGQSAASCHHAYIVLCIENSFMTASK
Endu-114
MGGSHHHHHHHSHRDFQPVLHLVALNSPLSGGMRGIRGADFQCFQQARAVGLAGTFRAFLSSRLQDLYSIVRR
ADRAAVPIVNLKDELLFPSWEALFSGSEGPLKPGARIFSFDGRDVLRHPTWPQKSVWHGSDPSGHRLTESYCET
WRTDSRAATGQASSLLGGRLLGQSAASCHHAYIVLCIANSFMTASK
Endu-57
MGGSHHHHHHHTHQDFHPVLHLVALNTPLSGGMRGIRGADFQCFQQARAVGLSGTFRAFLSSRLQDLYSIVRR
ADRAAVPIVNLKDELLFPSWEALFSGESGAGKTGGARIFSFDGRDVLRHPAWPQKSVWHGSDPSGRRLTESYC
ETWRTDSRAATGQASSLLAGRLLEQKAAGCHNAFIVLCIENSFMTSSSK

Figure 37

SEQUENCE LISTING

<160> NUMBER OF SEQ ID NOS: 39

<210> SEQ ID NO 1
<211> LENGTH: 183
<212> TYPE: PRT
<213> ORGANISM: Homo sapiens

<400> SEQUENCE: 1

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
                20                  25                  30

Cys Phe Gln Gln Ala Arg Ala Val Gly Leu Ala Gly Thr Phe Arg Ala
            35                  40                  45

Phe Leu Ser Ser Arg Leu Gln Asp Leu Tyr Ser Ile Val Arg Arg Ala
        50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180

```
<210> SEQ ID NO 2
<211> LENGTH: 192
<212> TYPE: PRT
<213> ORGANISM: artificial sequence
<220> FEATURE:
<223> OTHER INFORMATION: mutant

<400> SEQUENCE: 2
```

Met Gly Gly Ser His His His His His Ser His Arg Asp Phe Gln
1               5                   10                  15

Pro Val Leu His Leu Val Ala Leu Asn Ser Pro Leu Ser Gly Gly Met
            20                  25                  30

Arg Gly Ile Arg Gly Ala Asp Phe Gln Cys Phe Gln Gln Ala Arg Ala
        35                  40                  45

Val Gly Leu Ala Gly Thr Phe Arg Ala Phe Leu Ser Ser Arg Leu Gln
50                  55                  60

Asp Leu Tyr Ser Ile Val Arg Arg Ala Asp Arg Ala Ala Val Pro Ile
65                  70                  75                  80

Val Asn Leu Lys Asp Glu Leu Leu Phe Pro Ser Trp Glu Ala Leu Phe
                85                  90                  95

Ser Gly Ser Glu Gly Pro Leu Lys Pro Gly Ala Arg Ile Phe Ser Phe
            100                 105                 110

Asp Gly Lys Asp Val Leu Arg His Pro Thr Trp Pro Gln Lys Ser Val
        115                 120                 125

Trp His Gly Ser Asp Pro Asn Gly Arg Arg Leu Thr Glu Ser Tyr Cys
130                 135                 140

Glu Thr Trp Arg Thr Glu Ala Pro Ser Ala Thr Gly Gln Ala Ser Ser
145                 150                 155                 160

Leu Leu Gly Gly Arg Leu Leu Gly Gln Ser Ala Ala Ser Cys His His
                165                 170                 175

Ala Tyr Ile Val Leu Cys Ile Glu Asn Ser Phe Met Thr Ala Ser Lys
            180                 185                 190

```
<210> SEQ ID NO 3
<211> LENGTH: 180
<212> TYPE: PRT
<213> ORGANISM: artificial sequence
<220> FEATURE:
<223> OTHER INFORMATION: mutant

<400> SEQUENCE: 3
```

Asp Phe Gln Pro Val Leu His Leu Val Ala Leu Asn Ser Pro Leu Ser
1               5                   10                  15

Gly Gly Met Arg Gly Ile Arg Gly Ala Asp Phe Gln Cys Phe Gln Gln
            20                  25                  30

Ala Arg Ala Val Gly Leu Ala Gly Thr Phe Arg Ala Phe Leu Ser Ser
        35                  40                  45

Arg Leu Gln Asp Leu Tyr Ser Ile Val Arg Arg Ala Asp Arg Ala Ala
    50                  55                  60

Val Pro Ile Val Asn Leu Lys Asp Glu Leu Leu Phe Pro Ser Trp Glu
65                  70                  75                  80

Ala Leu Phe Ser Gly Glu Ser Gly Ala Gly Lys Thr Pro Gly Ala Arg
                85                  90                  95

Ile Phe Ser Phe Asp Gly Lys Asp Val Leu Arg His Pro Thr Trp Pro
            100                 105                 110

Gln Lys Ser Val Trp His Gly Ser Asp Pro Asn Gly Arg Arg Leu Thr
        115                 120                 125

```
Glu Ser Tyr Cys Glu Thr Trp Arg Thr Glu Ala Pro Ser Ala Thr Gly
130                 135                 140

Gln Ala Ser Ser Leu Leu Gly Gly Arg Leu Leu Gly Gln Ser Ala Ala
145                 150                 155                 160

Ser Cys His His Ala Tyr Ile Val Leu Cys Ile Glu Asn Ser Phe Met
                165                 170                 175

Thr Ala Ser Lys
            180

<210> SEQ ID NO 4
<211> LENGTH: 171
<212> TYPE: PRT
<213> ORGANISM: artificial sequence
<220> FEATURE:
<223> OTHER INFORMATION: mutant

<400> SEQUENCE: 4

Asp Phe Gln Pro Val Leu His Leu Val Ala Leu Asn Ser Pro Leu Ser
1               5                   10                  15

Gly Gly Met Arg Gly Ile Arg Gly Ala Asp Phe Gln Cys Phe Gln Gln
                20                  25                  30

Ala Arg Ala Val Gly Leu Ala Gly Thr Phe Arg Ala Phe Leu Ser Ser
            35                  40                  45

Arg Leu Gln Asp Leu Tyr Ser Ile Val Arg Arg Ala Asp Arg Ala Ala
        50                  55                  60

Val Pro Ile Val Asn Leu Lys Asp Glu Leu Leu Phe Pro Ser Trp Glu
65                  70                  75                  80

Ala Leu Phe Ser Gly Ser Glu Gly Pro Leu Lys Ser Pro Gly Ala Arg
                85                  90                  95

Ile Phe Ser Phe Asp Gly Lys Asp Val Leu Arg His Pro Thr Trp Pro
                100                 105                 110

Gln Lys Ser Val Trp His Gly Ser Asp Pro Asn Gly Arg Arg Leu Thr
            115                 120                 125

Glu Ser Tyr Cys Glu Thr Trp Arg Thr Glu Ala Pro Ser Ala Thr Gly
130                 135                 140

Gln Ala Ser Ser Leu Leu Gly Gly Arg Leu Leu Gly Gln Ser Ala Ala
145                 150                 155                 160

Ser Cys His His Ala Tyr Ile Val Leu Cys Ile
                165                 170

<210> SEQ ID NO 5
<211> LENGTH: 171
<212> TYPE: PRT
<213> ORGANISM: artificial sequence
<220> FEATURE:
<223> OTHER INFORMATION: mutant

<400> SEQUENCE: 5

Asp Phe Gln Pro Val Leu His Leu Val Ala Leu Asn Ser Pro Leu Ser
1               5                   10                  15

Gly Gly Met Arg Gly Ile Arg Gly Ala Asp Phe Gln Cys Phe Gln Gln
                20                  25                  30

Ala Arg Ala Val Gly Leu Ala Gly Thr Phe Arg Ala Phe Leu Ser Ser
            35                  40                  45

Arg Leu Gln Asp Leu Tyr Ser Ile Val Arg Arg Ala Asp Arg Ala Ala
        50                  55                  60

Val Pro Ile Val Asn Leu Lys Asp Glu Leu Leu Phe Pro Ser Trp Glu
65                  70                  75                  80
```

Ala Leu Phe Ser Gly Ser Glu Gly Pro Leu Lys Thr Pro Gly Ala Arg
            85                  90                  95

Ile Phe Ser Phe Asp Gly Lys Asp Val Leu Arg His Pro Thr Trp Pro
            100                 105                 110

Gln Lys Ser Val Trp His Gly Ser Asp Pro Asn Gly Arg Arg Leu Thr
            115                 120                 125

Glu Ser Tyr Cys Glu Thr Trp Arg Thr Glu Ala Pro Ser Ala Thr Gly
        130                 135                 140

Gln Ala Ser Ser Leu Leu Gly Gly Arg Leu Leu Gly Gln Ser Ala Ala
145                 150                 155                 160

Ser Cys His His Ala Tyr Ile Val Leu Cys Ile
            165                 170

<210> SEQ ID NO 6
<211> LENGTH: 171
<212> TYPE: PRT
<213> ORGANISM: artificial sequence
<220> FEATURE:
<223> OTHER INFORMATION: mutant

<400> SEQUENCE: 6

Asp Phe Gln Pro Val Leu His Leu Val Ala Leu Asn Ser Pro Leu Ser
1               5                   10                  15

Gly Gly Met Arg Gly Ile Arg Gly Ala Asp Phe Gln Cys Phe Gln Gln
            20                  25                  30

Ala Arg Ala Val Gly Leu Ala Gly Thr Phe Arg Ala Phe Leu Ser Ser
            35                  40                  45

Arg Leu Gln Asp Leu Tyr Ser Ile Val Arg Arg Ala Asp Arg Ala Ala
        50                  55                  60

Val Pro Ile Val Asn Leu Lys Asp Glu Leu Leu Phe Pro Ser Trp Glu
65                  70                  75                  80

Ala Leu Phe Ser Gly Glu Ser Gly Ala Gly Lys Thr Pro Gly Ala Arg
            85                  90                  95

Ile Phe Ser Phe Asp Gly Lys Asp Val Leu Arg His Pro Thr Trp Pro
            100                 105                 110

Gln Lys Ser Val Trp His Gly Ser Asp Pro Asn Gly Arg Arg Leu Thr
            115                 120                 125

Glu Ser Tyr Cys Glu Thr Trp Arg Thr Glu Ala Pro Ser Ala Thr Gly
        130                 135                 140

Gln Ala Ser Ser Leu Leu Gly Gly Arg Leu Leu Gly Gln Ser Ala Ala
145                 150                 155                 160

Ser Cys His His Ala Tyr Ile Val Leu Cys Ile
            165                 170

<210> SEQ ID NO 7
<211> LENGTH: 177
<212> TYPE: PRT
<213> ORGANISM: artificial sequence
<220> FEATURE:
<223> OTHER INFORMATION: mutant

<400> SEQUENCE: 7

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
            35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Glu Ser Gly Ala Gly Lys Thr
                85                  90                  95

Pro Gly Ala Arg Ile Phe Ser Phe Asp Gly Lys Asp Val Leu Arg His
                100                 105                 110

Pro Thr Trp Pro Gln Lys Ser Val Trp His Gly Ser Asp Pro Asn Gly
                115                 120                 125

Arg Arg Leu Thr Glu Ser Tyr Cys Glu Thr Trp Arg Thr Glu Ala Pro
130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn

<210> SEQ ID NO 8
<211> LENGTH: 180
<212> TYPE: PRT
<213> ORGANISM: artificial sequence
<220> FEATURE:
<223> OTHER INFORMATION: mutant

<400> SEQUENCE: 8

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Glu Ser Gly Ala Gly Lys Thr
                85                  90                  95

Pro Gly Ala Arg Ile Phe Ser Phe Asp Gly Lys Asp Val Leu Arg His
                100                 105                 110

Pro Thr Trp Pro Gln Lys Ser Val Trp His Gly Ser Asp Pro Asn Gly
                115                 120                 125

Arg Arg Leu Thr Glu Ser Tyr Cys Glu Thr Trp Arg Thr Glu Ala Pro
130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met
            180

<210> SEQ ID NO 9
<211> LENGTH: 176
<212> TYPE: PRT
<213> ORGANISM: artificial sequence
<220> FEATURE:
<223> OTHER INFORMATION: mutant

```
<400> SEQUENCE: 9

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

<210> SEQ ID NO 10
<211> LENGTH: 175
<212> TYPE: PRT
<213> ORGANISM: artificial sequence
<220> FEATURE:
<223> OTHER INFORMATION: mutant

<400> SEQUENCE: 10

His Arg Asp Phe Gln Pro Val Leu His Leu Val Ala Leu Asn Ser Pro
1               5                   10                  15

Leu Ser Gly Gly Met Arg Gly Ile Arg Gly Ala Asp Phe Gln Cys Phe
            20                  25                  30

Gln Gln Ala Arg Ala Val Gly Leu Ala Gly Thr Phe Arg Ala Phe Leu
        35                  40                  45

Ser Ser Arg Leu Gln Asp Leu Tyr Ser Ile Val Arg Arg Ala Asp Arg
    50                  55                  60

Ala Ala Val Pro Ile Val Asn Leu Lys Asp Glu Leu Leu Phe Pro Ser
65                  70                  75                  80

Trp Glu Ala Leu Phe Ser Gly Ser Glu Gly Ala Gly Lys Thr Pro Gly
                85                  90                  95

Ala Arg Ile Phe Ser Phe Asp Gly Lys Asp Val Leu Arg His Pro Thr
            100                 105                 110

Trp Pro Gln Lys Ser Val Trp His Gly Ser Asp Pro Asn Gly Arg Arg
        115                 120                 125

Leu Thr Glu Ser Tyr Cys Glu Thr Trp Arg Thr Glu Ala Pro Ser Ala
    130                 135                 140

Thr Gly Gln Ala Ser Ser Leu Leu Gly Gly Arg Leu Leu Gly Gln Ser
145                 150                 155                 160

Ala Ala Ser Cys His His Ala Tyr Ile Val Leu Cys Ile Glu Asn
                165                 170                 175
```

<210> SEQ ID NO 11
<211> LENGTH: 178
<212> TYPE: PRT
<213> ORGANISM: artificial sequence
<220> FEATURE:
<223> OTHER INFORMATION: mutant

<400> SEQUENCE: 11

His Arg Asp Phe Gln Pro Val Leu His Leu Val Ala Leu Asn Ser Pro
1               5                   10                  15

Leu Ser Gly Gly Met Arg Gly Ile Arg Gly Ala Asp Phe Gln Cys Phe
            20                  25                  30

Gln Gln Ala Arg Ala Val Gly Leu Ala Gly Thr Phe Arg Ala Phe Leu
        35                  40                  45

Ser Ser Arg Leu Gln Asp Leu Tyr Ser Ile Val Arg Arg Ala Asp Arg
    50                  55                  60

Ala Ala Val Pro Ile Val Asn Leu Lys Asp Glu Leu Leu Phe Pro Ser
65                  70                  75                  80

Trp Glu Ala Leu Phe Ser Gly Glu Ser Gly Ala Gly Lys Thr Pro Gly
                85                  90                  95

Ala Arg Ile Phe Ser Phe Asp Gly Lys Asp Val Leu Arg His Pro Thr
            100                 105                 110

Trp Pro Gln Lys Ser Val Trp His Gly Ser Asp Pro Asn Gly Arg Arg
        115                 120                 125

Leu Thr Glu Ser Tyr Cys Glu Thr Trp Arg Thr Glu Ala Pro Ser Ala
    130                 135                 140

Thr Gly Gln Ala Ser Ser Leu Leu Gly Gly Arg Leu Leu Gly Gln Ser
145                 150                 155                 160

Ala Ala Ser Cys His His Ala Tyr Ile Val Leu Cys Ile Glu Asn Ser
                165                 170                 175

Phe Met

<210> SEQ ID NO 12
<211> LENGTH: 181
<212> TYPE: PRT
<213> ORGANISM: artificial sequence
<220> FEATURE:
<223> OTHER INFORMATION: mutant

<400> SEQUENCE: 12

His Arg Asp Phe Gln Pro Val Leu His Leu Val Ala Leu Asn Ser Pro
1               5                   10                  15

Leu Ser Gly Gly Met Arg Gly Ile Arg Gly Ala Asp Phe Gln Cys Phe
            20                  25                  30

Gln Gln Ala Arg Ala Val Gly Leu Ala Gly Thr Phe Arg Ala Phe Leu
        35                  40                  45

Ser Ser Arg Leu Gln Asp Leu Tyr Ser Ile Val Arg Arg Ala Asp Arg
    50                  55                  60

Ala Ala Val Pro Ile Val Asn Leu Lys Asp Glu Leu Leu Phe Pro Ser
65                  70                  75                  80

Trp Glu Ala Leu Phe Ser Gly Glu Ser Gly Ala Gly Lys Thr Pro Gly
                85                  90                  95

Ala Arg Ile Phe Ser Phe Asp Gly Lys Asp Val Leu Arg His Pro Thr
            100                 105                 110

Trp Pro Gln Lys Ser Val Trp His Gly Ser Asp Pro Asn Gly Arg Arg
        115                 120                 125

```
Leu Thr Glu Ser Tyr Cys Glu Thr Trp Arg Thr Glu Ala Pro Ser Ala
        130                 135                 140

Thr Gly Gln Ala Ser Ser Leu Leu Gly Gly Arg Leu Leu Gly Gln Ser
145                 150                 155                 160

Ala Ala Ser Cys His His Ala Tyr Ile Val Leu Cys Ile Glu Asn Ser
                165                 170                 175

Phe Met Thr Ala Ser
            180

<210> SEQ ID NO 13
<211> LENGTH: 182
<212> TYPE: PRT
<213> ORGANISM: artificial sequence
<220> FEATURE:
<223> OTHER INFORMATION: mutant

<400> SEQUENCE: 13

Ser His Arg Asp Phe Gln Pro Val Leu His Leu Val Ala Leu Asn Ser
1               5                   10                  15

Pro Leu Ser Gly Gly Met Arg Gly Ile Arg Gly Ala Asp Phe Gln Cys
            20                  25                  30

Phe Gln Gln Ala Arg Ala Val Gly Leu Ala Gly Thr Phe Arg Ala Phe
        35                  40                  45

Leu Ser Ser Arg Leu Gln Asp Leu Tyr Ser Ile Val Arg Arg Ala Asp
    50                  55                  60

Arg Ala Ala Val Pro Ile Val Asn Leu Lys Asp Glu Leu Leu Phe Pro
65                  70                  75                  80

Ser Trp Glu Ala Leu Phe Ser Gly Glu Ser Gly Ala Gly Lys Thr Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser
            180

<210> SEQ ID NO 14
<211> LENGTH: 176
<212> TYPE: PRT
<213> ORGANISM: artificial sequence
<220> FEATURE:
<223> OTHER INFORMATION: mutant

<400> SEQUENCE: 14

Ser His Arg Asp Phe Gln Pro Val Leu His Leu Val Ala Leu Asn Ser
1               5                   10                  15

Pro Leu Ser Gly Gly Met Arg Gly Ile Arg Gly Ala Asp Phe Gln Cys
            20                  25                  30

Phe Gln Gln Ala Arg Ala Val Gly Leu Ala Gly Thr Phe Arg Ala Phe
        35                  40                  45
```

```
Leu Ser Ser Arg Leu Gln Asp Leu Tyr Ser Ile Val Arg Arg Ala Asp
 50                  55                  60

Arg Ala Ala Val Pro Ile Val Asn Leu Lys Asp Glu Leu Leu Phe Pro
 65                  70                  75                  80

Ser Trp Glu Ala Leu Phe Ser Gly Glu Ser Gly Ala Gly Lys Thr Pro
                 85                  90                  95

Gly Ala Arg Ile Phe Ser Phe Asp Gly Lys Asp Val Leu Arg His Pro
                100                 105                 110

Thr Trp Pro Gln Lys Ser Val Trp His Gly Ser Asp Pro Asn Gly Arg
                115                 120                 125

Arg Leu Thr Glu Ser Tyr Cys Glu Thr Trp Arg Thr Glu Ala Pro Ser
                130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175
```

<210> SEQ ID NO 15
<211> LENGTH: 179
<212> TYPE: PRT
<213> ORGANISM: artificial sequence
<220> FEATURE:
<223> OTHER INFORMATION: mutant

<400> SEQUENCE: 15

```
Ser His Arg Asp Phe Gln Pro Val Leu His Leu Val Ala Leu Asn Ser
 1               5                  10                  15

Pro Leu Ser Gly Gly Met Arg Gly Ile Arg Gly Ala Asp Phe Gln Cys
                 20                  25                  30

Phe Gln Gln Ala Arg Ala Val Gly Leu Ala Gly Thr Phe Arg Ala Phe
                 35                  40                  45

Leu Ser Ser Arg Leu Gln Asp Leu Tyr Ser Ile Val Arg Arg Ala Asp
 50                  55                  60

Arg Ala Ala Val Pro Ile Val Asn Leu Lys Asp Glu Leu Leu Phe Pro
 65                  70                  75                  80

Ser Trp Glu Ala Leu Phe Ser Gly Glu Ser Gly Ala Gly Lys Thr Pro
                 85                  90                  95

Gly Ala Arg Ile Phe Ser Phe Asp Gly Lys Asp Val Leu Arg His Pro
                100                 105                 110

Thr Trp Pro Gln Lys Ser Val Trp His Gly Ser Asp Pro Asn Gly Arg
                115                 120                 125

Arg Leu Thr Glu Ser Tyr Cys Glu Thr Trp Arg Thr Glu Ala Pro Ser
                130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met
```

<210> SEQ ID NO 16
<211> LENGTH: 183
<212> TYPE: PRT
<213> ORGANISM: artificial sequence
<220> FEATURE:
<223> OTHER INFORMATION: mutant

<400> SEQUENCE: 16

Ser His Arg Asp Phe Gln Pro Val Leu His Leu Val Ala Leu Asn Ser
1               5                   10                  15

Pro Leu Ser Gly Gly Met Arg Gly Ile Arg Gly Ala Asp Phe Gln Cys
            20                  25                  30

Phe Gln Gln Ala Arg Ala Val Gly Leu Ala Gly Thr Phe Arg Ala Phe
        35                  40                  45

Leu Ser Ser Arg Leu Gln Asp Leu Tyr Ser Ile Val Arg Arg Ala Asp
    50                  55                  60

Arg Ala Ala Val Pro Ile Val Asn Leu Lys Asp Glu Leu Leu Phe Pro
65                  70                  75                  80

Ser Trp Glu Ala Leu Phe Ser Gly Glu Ser Gly Ala Gly Lys Thr Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180

<210> SEQ ID NO 17
<211> LENGTH: 182
<212> TYPE: PRT
<213> ORGANISM: artificial sequence
<220> FEATURE:
<223> OTHER INFORMATION: mutant

<400> SEQUENCE: 17

His Arg Asp Phe Gln Pro Val Leu His Leu Val Ala Leu Asn Ser Pro
1               5                   10                  15

Leu Ser Gly Gly Met Arg Gly Ile Arg Gly Ala Asp Phe Gln Cys Phe
            20                  25                  30

Gln Gln Ala Arg Ala Val Gly Leu Ala Gly Thr Phe Arg Ala Phe Leu
        35                  40                  45

Ser Ser Arg Leu Gln Asp Leu Tyr Ser Ile Val Arg Arg Ala Asp Arg
    50                  55                  60

Ala Ala Val Pro Ile Val Asn Leu Lys Asp Glu Leu Leu Phe Pro Ser
65                  70                  75                  80

Trp Glu Ala Leu Phe Ser Gly Glu Ser Gly Ala Gly Lys Thr Pro Gly
                85                  90                  95

Ala Arg Ile Phe Ser Phe Asp Gly Lys Asp Val Leu Arg His Pro Thr
            100                 105                 110

Trp Pro Gln Lys Ser Val Trp His Gly Ser Asp Pro Asn Gly Arg Arg
        115                 120                 125

Leu Thr Glu Ser Tyr Cys Glu Thr Trp Arg Thr Glu Ala Pro Ser Ala
    130                 135                 140

Thr Gly Gln Ala Ser Ser Leu Leu Gly Gly Arg Leu Leu Gly Gln Ser
145                 150                 155                 160

```
Ala Ala Ser Cys His His Ala Tyr Ile Val Leu Cys Ile Glu Asn Ser
                165                 170                 175
Phe Met Thr Ala Ser Lys
            180
```

<210> SEQ ID NO 18
<211> LENGTH: 183
<212> TYPE: PRT
<213> ORGANISM: artificial sequence
<220> FEATURE:
<223> OTHER INFORMATION: mutant

<400> SEQUENCE: 18

```
His Ser His Arg Asp Phe Gln Pro Val Leu His Leu Val Ala Leu Asn
1               5                   10                  15
Ser Pro Leu Ser Gly Gly Met Arg Gly Ile Arg Gly Ala Asp Phe Gln
            20                  25                  30
Cys Phe Gln Gln Ala Arg Ala Val Gly Leu Ala Gly Thr Phe Arg Ala
        35                  40                  45
Phe Leu Ser Ser Arg Leu Gln Asp Leu Tyr Ser Ile Val Arg Arg Ala
    50                  55                  60
Asp Arg Ala Ala Val Pro Ile Val Asn Leu Lys Asp Glu Leu Leu Phe
65                  70                  75                  80
Pro Ser Trp Glu Ala Leu Phe Gly Glu Ser Gly Ala Gly Lys Thr Pro
                85                  90                  95
Gly Ala Arg Ile Phe Ser Phe Asp Gly Lys Asp Val Leu Arg His Pro
            100                 105                 110
Thr Trp Pro Gln Lys Ser Val Trp His Gly Ser Asp Pro Asn Gly Arg
        115                 120                 125
Arg Leu Thr Glu Ser Tyr Cys Glu Thr Trp Arg Thr Glu Ala Pro Ser
    130                 135                 140
Ala Thr Gly Gln Ala Ser Ser Leu Leu Gly Gly Arg Leu Leu Gly Gln
145                 150                 155                 160
Ser Ala Ala Ser Cys His His Ala Tyr Ile Val Leu Cys Ile Glu Asn
                165                 170                 175
Ser Phe Met Thr Ala Ser Lys
            180
```

<210> SEQ ID NO 19
<211> LENGTH: 183
<212> TYPE: PRT
<213> ORGANISM: artificial sequence
<220> FEATURE:
<223> OTHER INFORMATION: mutant

<400> SEQUENCE: 19

```
His Ser His Arg Asp Phe Gln Pro Val Leu His Leu Val Ala Leu Asn
1               5                   10                  15
Ser Pro Leu Ser Gly Gly Met Arg Gly Ile Arg Gly Ala Asp Phe Gln
            20                  25                  30
Cys Phe Gln Gln Ala Arg Ala Val Gly Leu Ala Gly Thr Phe Arg Ala
        35                  40                  45
Phe Leu Ser Ser Arg Leu Gln Asp Leu Tyr Ser Ile Val Arg Arg Ala
    50                  55                  60
Asp Arg Ala Ala Val Pro Ile Val Asn Leu Lys Asp Glu Leu Leu Phe
65                  70                  75                  80
Pro Ser Trp Glu Ala Leu Phe Ser Gly Glu Ser Gly Ala Gly Lys Thr
                85                  90                  95
```

```
Pro Ala Arg Ile Phe Ser Phe Asp Gly Lys Asp Val Leu Arg His Pro
                100                 105                 110

Thr Trp Pro Gln Lys Ser Val Trp His Gly Ser Asp Pro Asn Gly Arg
            115                 120                 125

Arg Leu Thr Glu Ser Tyr Cys Glu Thr Trp Arg Thr Glu Ala Pro Ser
        130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180

<210> SEQ ID NO 20
<211> LENGTH: 183
<212> TYPE: PRT
<213> ORGANISM: artificial sequence
<220> FEATURE:
<223> OTHER INFORMATION: mutant

<400> SEQUENCE: 20

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Glu Ser Gly Ala Gly Lys Thr
                85                  90                  95

Gly Ala Arg Ile Phe Ser Phe Asp Gly Lys Asp Val Leu Arg His Pro
                100                 105                 110

Thr Trp Pro Gln Lys Ser Val Trp His Gly Ser Asp Pro Asn Gly Arg
            115                 120                 125

Arg Leu Thr Glu Ser Tyr Cys Glu Thr Trp Arg Thr Glu Ala Pro Ser
        130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180

<210> SEQ ID NO 21
<211> LENGTH: 184
<212> TYPE: PRT
<213> ORGANISM: artificial sequence
<220> FEATURE:
<223> OTHER INFORMATION: mutant

<400> SEQUENCE: 21

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30
```

Cys Phe Gln Gln Ala Arg Ala Val Gly Leu Ala Gly Thr Phe Arg Ala
            35                  40                  45

Phe Leu Ser Ser Arg Leu Gln Asp Leu Tyr Ser Ile Val Arg Arg Ala
 50                  55                  60

Asp Arg Ala Ala Val Pro Ile Val Asn Leu Lys Asp Glu Leu Leu Phe
 65                  70                  75                  80

Pro Ser Trp Glu Ala Leu Phe Ser Gly Glu Ser Gly Ala Gly Lys Thr
                 85                  90                  95

Gly Gly Ala Arg Ile Phe Ser Phe Asp Gly Lys Asp Val Leu Arg His
                100                 105                 110

Pro Thr Trp Pro Gln Lys Ser Val Trp His Gly Ser Asp Pro Asn Gly
                115                 120                 125

Arg Arg Leu Thr Glu Ser Tyr Cys Glu Thr Trp Arg Thr Glu Ala Pro
            130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Lys
            180

<210> SEQ ID NO 22
<211> LENGTH: 183
<212> TYPE: PRT
<213> ORGANISM: artificial sequence
<220> FEATURE:
<223> OTHER INFORMATION: mutant

<400> SEQUENCE: 22

His Ser His Arg Asp Phe Gln Pro Val Leu His Leu Val Ala Leu Asn
 1               5                  10                  15

Ser Pro Leu Ser Gly Gly Met Arg Gly Ile Arg Gly Ala Asp Phe Gln
             20                  25                  30

Cys Phe Gln Gln Ala Arg Ala Val Gly Leu Ala Gly Thr Phe Arg Ala
            35                  40                  45

Phe Leu Ser Ser Arg Leu Gln Asp Leu Tyr Ser Ile Val Arg Arg Ala
 50                  55                  60

Asp Arg Ala Ala Val Pro Ile Val Asn Leu Lys Asp Glu Leu Leu Phe
 65                  70                  75                  80

Pro Ser Trp Glu Ala Leu Phe Ser Gly Ser Glu Gly Pro Leu Lys Pro
                 85                  90                  95

Gly Ala Arg Ile Phe Ser Phe Asp Gly Lys Asp Val Leu Arg His Pro
                100                 105                 110

Thr Trp Pro Gln Lys Ser Val Trp His Gly Ser Asp Pro Asn Gly Arg
            115                 120                 125

Arg Leu Thr Glu Ser Tyr Cys Glu Thr Trp Arg Thr Glu Ala Pro Ser
            130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Ala Asn
                165                 170                 175

Ser Phe Met Thr Ala Ser Lys
            180

-continued

```
<210> SEQ ID NO 23
<211> LENGTH: 183
<212> TYPE: PRT
<213> ORGANISM: artificial sequence
<220> FEATURE:
<223> OTHER INFORMATION: mutant

<400> SEQUENCE: 23
```

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Glu Ile Glu Asn
                165                 170                 175

Ser Phe Met Thr Ala Ser Lys
            180

```
<210> SEQ ID NO 24
<211> LENGTH: 184
<212> TYPE: PRT
<213> ORGANISM: artificial sequence
<220> FEATURE:
<223> OTHER INFORMATION: mutant

<400> SEQUENCE: 24
```

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Glu Ser Gly Ala Gly Lys Thr
                85                  90                  95

Pro Gly Ala Arg Ile Phe Ser Phe Asp Gly Lys Asp Val Leu Arg His
            100                 105                 110

Pro Thr Trp Pro Gln Lys Ser Val Trp His Gly Ser Asp Pro Asn Gly
        115                 120                 125

```
Arg Arg Leu Thr Glu Ser Tyr Cys Glu Thr Trp Arg Thr Glu Ala Pro
130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Lys
            180
```

<210> SEQ ID NO 25
<211> LENGTH: 179
<212> TYPE: PRT
<213> ORGANISM: artificial sequence
<220> FEATURE:
<223> OTHER INFORMATION: mutant

<400> SEQUENCE: 25

```
Arg Asp Phe Gln Pro Val Leu His Leu Val Ala Leu Asn Ser Pro Leu
1               5                   10                  15

Ser Gly Gly Met Arg Gly Ile Arg Gly Ala Asp Phe Gln Cys Phe Gln
                20                  25                  30

Gln Ala Arg Gln Val Gly Leu Ala Gly Thr Phe Arg Ala Phe Leu Ser
            35                  40                  45

Ser Arg Leu Gln Asp Leu Tyr Ser Ile Val Arg Arg Ala Asp Arg Ala
50                  55                  60

Ala Val Pro Ile Val Asn Leu Lys Asp Glu Leu Leu Phe Pro Ser Trp
65                  70                  75                  80

Glu Ala Leu Phe Ser Ser Glu Gly Pro Leu Lys Pro Gly Ala Arg Ile
                85                  90                  95

Phe Ser Phe Asp Gly Lys Asp Val Leu Arg His Pro Thr Trp Pro Gln
            100                 105                 110

Lys Ser Val Trp His Gly Ser Asp Pro Asn Gly Arg Arg Leu Thr Glu
        115                 120                 125

Ser Tyr Cys Glu Thr Trp Arg Thr Glu Ala Pro Ser Ala Thr Gly Gln
130                 135                 140

Ala Ser Ser Leu Leu Gly Gly Arg Leu Leu Gly Gln Ser Ala Ala Ser
145                 150                 155                 160

Cys His His Ala Tyr Ile Val Leu Cys Ile Glu Asn Ser Phe Met Thr
                165                 170                 175

Ala Ser Lys
```

<210> SEQ ID NO 26
<211> LENGTH: 180
<212> TYPE: PRT
<213> ORGANISM: artificial sequence
<220> FEATURE:
<223> OTHER INFORMATION: mutant

<400> SEQUENCE: 26

```
Arg Asp Phe Gln Pro Val Leu His Leu Val Ala Leu Asn Ser Pro Leu
1               5                   10                  15

Ser Gly Gly Met Arg Gly Ile Arg Gly Ala Asp Phe Gln Cys Phe Gln
                20                  25                  30

Gln Ala Arg Ala Val Gly Leu Ala Gly Thr Phe Arg Ala Phe Leu Ser
            35                  40                  45

Ser Arg Leu Gln Asp Leu Tyr Ser Ile Val Arg Arg Ala Asp Arg Gly
50                  55                  60
```

```
Ser Val Pro Ile Val Asn Leu Lys Asp Glu Val Leu Ser Pro Ser Trp
 65                  70                  75                  80

Asp Ser Leu Phe Ser Gly Ser Gln Gly Gln Leu Gln Pro Gly Ala Arg
                 85                  90                  95

Ile Phe Ser Phe Asp Gly Arg Asp Ile Leu Gln Asp Ser Ala Trp Pro
            100                 105                 110

Gln Lys Ser Val Trp His Gly Ser Asp Ala Lys Gly Arg Arg Leu Pro
        115                 120                 125

Glu Ser Tyr Cys Glu Ala Trp Arg Thr Asp Glu Arg Gly Thr Ser Gly
    130                 135                 140

Gln Ala Ser Ser Leu Leu Ser Gly Arg Leu Leu Glu Gln Lys Ala Ala
145                 150                 155                 160

Ser Cys His Asn Ser Tyr Ile Val Leu Cys Ile Glu Asn Ser Phe Met
                165                 170                 175

Thr Ala Ser Lys
            180

<210> SEQ ID NO 27
<211> LENGTH: 184
<212> TYPE: PRT
<213> ORGANISM: artificial sequence
<220> FEATURE:
<223> OTHER INFORMATION: mutant

<400> SEQUENCE: 27

His Val His Gln Asp Phe Gln Pro Ala Leu His Leu Val Ala Leu Asn
  1               5                  10                  15

Thr Pro Leu Ser Gly Gly Met Arg Gly Ile Arg Gly Ala Asp Phe Gln
             20                  25                  30

Cys Phe Gln Gln Ala Arg Gln Val Gly Leu Ala Gly Thr Phe Arg Ala
         35                  40                  45

Phe Leu Ser Ser Arg Leu Gln Asp Leu Tyr Ser Ile Val Arg Arg Ala
     50                  55                  60

Asp Arg Thr Ala Val Pro Ile Val Asn Leu Arg Asp Glu Val Leu Phe
 65                  70                  75                  80

Ser Asn Trp Glu Ala Leu Phe Thr Gly Ser Glu Ala Pro Leu Arg Ala
                 85                  90                  95

Gly Ala Arg Ile Phe Ser Phe Asp Gly Arg Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Ala Gly Arg Leu Leu Glu Gln
145                 150                 155                 160

Lys Ala Ala Gly Cys His Asn Ala Phe Ile Val Leu Cys Ile Glu Asn
                165                 170                 175

Ser Phe Met Thr Ser Ser Lys
            180

<210> SEQ ID NO 28
<211> LENGTH: 185
<212> TYPE: PRT
<213> ORGANISM: artificial sequence
<220> FEATURE:
<223> OTHER INFORMATION: mutant
```

```
<400> SEQUENCE: 28

His Thr His Gln Asp Phe His Pro Val Leu His Leu Val Ala Leu Asn
1               5                   10                  15

Thr Pro Leu Ser Gly Gly Met Arg Gly Ile Arg Gly Ala Asp Phe Gln
            20                  25                  30

Cys Phe Gln Gln Ala Arg Ala Val Gly Leu Ser Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Glu Ser Gly Ala Gly Lys Thr
                85                  90                  95

Gly Gly Ala Arg Ile Phe Ser Phe Asp Gly Arg Asp Val Leu Arg His
            100                 105                 110

Pro Ala Trp Pro Gln Lys Ser Val Trp His Gly Ser Asp Pro Ser Gly
        115                 120                 125

Arg Arg Leu Thr Glu Ser Tyr Cys Glu Thr Trp Arg Thr Asp Ser Arg
    130                 135                 140

Ala Ala Thr Gly Gln Ala Ser Ser Leu Leu Ala Gly Arg Leu Leu Glu
145                 150                 155                 160

Gln Lys Ala Ala Gly Cys His Asn Ala Phe Ile Val Leu Cys Ile Glu
                165                 170                 175

Asn Ser Phe Met Thr Ser Ser Lys
            180                 185

<210> SEQ ID NO 29
<211> LENGTH: 183
<212> TYPE: PRT
<213> ORGANISM: artificial sequence
<220> FEATURE:
<223> OTHER INFORMATION: mutant

<400> SEQUENCE: 29

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Arg Asp Val Leu Arg His Pro
            100                 105                 110

Thr Trp Pro Gln Lys Ser Val Trp His Gly Ser Asp Pro Ser Gly His
        115                 120                 125

Arg Leu Thr Glu Ser Tyr Cys Glu Thr Trp Arg Thr Asp Ser Arg Ala
    130                 135                 140

Ala Thr Gly Gln Ala Ser Ser Leu Leu Gly Gly Arg Leu Leu Gly Gln
145                 150                 155                 160
```

Ser Ala Ala Ser Cys His His Ala Tyr Ile Val Leu Cys Ile Ala Asn
              165                 170                 175

Ser Phe Met Thr Ala Ser Lys
            180

<210> SEQ ID NO 30
<211> LENGTH: 179
<212> TYPE: PRT
<213> ORGANISM: artificial sequence
<220> FEATURE:
<223> OTHER INFORMATION: mutant

<400> SEQUENCE: 30

Asp Phe Gln Pro Val Leu His Leu Val Ala Leu Asn Ser Pro Leu Ser
1               5                   10                  15

Gly Gly Met Arg Gly Ile Arg Gly Ala Asp Phe Gln Cys Phe Gln Gln
            20                  25                  30

Ala Arg Ala Val Gly Leu Ala Gly Thr Phe Arg Ala Phe Leu Ser Ser
        35                  40                  45

Arg Leu Gln Asp Leu Tyr Ser Ile Val Arg Arg Ala Asp Arg Ala Ala
    50                  55                  60

Val Pro Ile Val Asn Leu Lys Asp Glu Leu Leu Phe Pro Ser Trp Glu
65                  70                  75                  80

Ala Leu Phe Ser Gly Ser Glu Gly Pro Leu Arg Pro Gly Ala Arg Ile
                85                  90                  95

Phe Ser Phe Asp Gly Lys Asp Val Leu Arg His Pro Thr Leu Pro Gln
            100                 105                 110

Lys Ser Val Trp His Gly Ser Asp Pro Ser Gly Arg Arg Leu Thr Glu
        115                 120                 125

Ser Tyr Cys Glu Thr Trp Arg Thr Asp Ser Arg Ala Ala Thr Gly Gln
    130                 135                 140

Ala Ser Ser Leu Leu Gly Gly Arg Leu Leu Gly Gln Ser Ala Ala Ser
145                 150                 155                 160

Cys His His Ala Tyr Ile Val Leu Cys Ile Glu Asn Ser Phe Met Thr
                165                 170                 175

Ala Ser Lys

<210> SEQ ID NO 31
<211> LENGTH: 180
<212> TYPE: PRT
<213> ORGANISM: artificial sequence
<220> FEATURE:
<223> OTHER INFORMATION: mutant

<400> SEQUENCE: 31

Asp Phe Gln Pro Val Leu His Leu Val Ala Leu Asn Ser Pro Leu Ser
1               5                   10                  15

Gly Gly Met Arg Gly Ile Arg Gly Ala Asp Phe Gln Cys Phe Gln Gln
            20                  25                  30

Ala Arg Ala Val Gly Leu Ala Gly Thr Phe Arg Ala Phe Leu Ser Ser
        35                  40                  45

Arg Leu Gln Asp Leu Tyr Ser Ile Val Arg Arg Ala Asp Arg Ala Ala
    50                  55                  60

Val Pro Ile Val Asn Leu Lys Asp Glu Leu Leu Phe Pro Ser Trp Glu
65                  70                  75                  80

Ala Leu Phe Ser Gly Ser Glu Gly Pro Leu Arg Pro Gly Ala Arg Ile
                85                  90                  95

```
Phe Ser Phe Asp Gly Lys Asp Val Leu Arg His Pro Thr Leu Pro Gln
            100                 105                 110

Lys Ser Val Trp His Gly Ser Asp Pro Ser Gly Arg Arg Leu Thr Glu
            115                 120                 125

Ser Tyr Cys Glu Thr Trp Arg Thr Asp Ser Arg Ala Ala Thr Gly Gln
            130                 135                 140

Ala Ser Ser Leu Leu Gly Gly Arg Leu Leu Gly Gln Ser Ala Ala Ser
145                 150                 155                 160

Cys His His Ala Tyr Ile Val Leu Cys Ile Glu Asn Ser Phe Met Thr
                165                 170                 175

Ala Ser Lys Lys
            180

<210> SEQ ID NO 32
<211> LENGTH: 184
<212> TYPE: PRT
<213> ORGANISM: artificial sequence
<220> FEATURE:
<223> OTHER INFORMATION: mutant

<400> SEQUENCE: 32

His Thr His Gln Asp Phe His Pro Val Leu His Leu Val Ala Leu Asn
1               5                   10                  15

Thr Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Arg Asp Ile Leu Gln Asp Ser
            100                 105                 110

Ala Trp Pro Gln Lys Ser Val Trp His Gly Ser Asp Pro Asn Gly Arg
            115                 120                 125

Arg Leu Thr Glu Ser Tyr Cys Glu Thr Trp Arg Thr Glu Ala Pro Ser
            130                 135                 140

Ala Thr Gly Gln Ala Ser Ser Leu Ser Ser Gly Lys Leu Leu Glu Gln
145                 150                 155                 160

Ser Val Ser Ser Cys Gln His Ala Phe Val Leu Cys Ile Glu Asn
                165                 170                 175

Ser Phe Met Thr Ala Ala Lys Lys
            180

<210> SEQ ID NO 33
<211> LENGTH: 183
<212> TYPE: PRT
<213> ORGANISM: artificial sequence
<220> FEATURE:
<223> OTHER INFORMATION: mutant

<400> SEQUENCE: 33

Thr Pro Thr Trp Tyr Pro Arg Met Leu Arg Val Ala Ala Leu Asn Glu
1               5                   10                  15

Pro Ser Thr Gly Asp Leu Gln Gly Ile Arg Gly Ala Asp Phe Gln Cys
            20                  25                  30
```

```
Phe Gln Gln Ala Arg Ala Val Gly Leu Ser Gly Thr Phe Arg Ala Phe
            35                  40                  45

Leu Ser Ser Arg Leu Gln Asp Leu Tyr Ser Ile Val Arg Arg Ala Asp
        50                  55                  60

Arg Ala Ala Val Pro Ile Val Asn Leu Lys Asp Glu Val Leu Ser Pro
65                  70                  75                  80

Ser Trp Asp Ser Leu Phe Ser Gly Ser Gln Gly Gln Leu Gln Pro Gly
                85                  90                  95

Ala Arg Ile Phe Ser Phe Asp Gly Lys Asp Val Leu Arg His Pro Thr
            100                 105                 110

Trp Pro Gln Lys Ser Val Trp His Gly Ser Asp Pro Ser Gly Arg Arg
            115                 120                 125

Leu Met Glu Ser Tyr Cys Glu Thr Trp Arg Thr Glu Thr Thr Gly Ala
        130                 135                 140

Thr Gly Gln Ala Ser Ser Leu Leu Gly Gly Arg Leu Leu Gly Gln Ser
145                 150                 155                 160

Ala Ala Ser Cys His His Ala Tyr Ile Val Leu Cys Ile Glu Asn Ser
                165                 170                 175

Phe Met Thr Asn Asn Arg Lys
            180
```

<210> SEQ ID NO 34
<211> LENGTH: 182
<212> TYPE: PRT
<213> ORGANISM: artificial sequence
<220> FEATURE:
<223> OTHER INFORMATION: mutant

<400> SEQUENCE: 34

```
His Thr His Thr Ser Gly Pro Gly Leu His Leu Ile Ala Leu Asn Ser
1               5                   10                  15

Pro Gln Val Gly Asn Met Arg Gly Ile Arg Gly Ala Asp Phe Gln Cys
            20                  25                  30

Phe Gln Gln Ala Arg Ala Val Gly Leu Ala Gly Thr Phe Arg Ala Phe
            35                  40                  45

Leu Ser Ser Arg Leu Gln Asp Leu Tyr Ser Ile Val Arg Arg Ala Asp
        50                  55                  60

Arg Ser Ser Val Pro Ile Val Asn Leu Lys Asp Glu Val Leu Ser Pro
65                  70                  75                  80

Ser Trp Asp Ser Leu Phe Ser Val Ser Gln Gly Gln Leu Gln Pro Gly
                85                  90                  95

Ala Arg Ile Phe Ser Phe Asp Gly Arg Asp Ile Leu Gln Asp Ser Ala
            100                 105                 110

Trp Pro Gln Lys Ser Val Trp His Gly Ser Asp Pro Asn Gly Arg Arg
            115                 120                 125

Leu Thr Glu Ser Tyr Cys Glu Thr Trp Arg Thr Glu Ala Pro Ser Ala
        130                 135                 140

Thr Gly Gln Ala Ser Ser Leu Leu Gly Gly Arg Leu Leu Gly Gln Ser
145                 150                 155                 160

Ala Ala Ser Cys His His Ala Tyr Ile Val Leu Cys Ile Glu Asn Ser
                165                 170                 175

Phe Met Thr Ala Ser Lys
            180
```

-continued

<210> SEQ ID NO 35
<211> LENGTH: 31
<212> TYPE: DNA
<213> ORGANISM: artificial sequence
<220> FEATURE:
<223> OTHER INFORMATION: primer

<400> SEQUENCE: 35
ggaattccat atgcacagcc accgcgactt c                                31

<210> SEQ ID NO 36
<211> LENGTH: 34
<212> TYPE: DNA
<213> ORGANISM: artificial sequence
<220> FEATURE:
<223> OTHER INFORMATION: primer

<400> SEQUENCE: 36
ccgctcgagt tacttggagg cagtcatgaa gctg                             34

<210> SEQ ID NO 37
<211> LENGTH: 193
<212> TYPE: PRT
<213> ORGANISM: artificial sequence
<220> FEATURE:
<223> OTHER INFORMATION: mutant

<400> SEQUENCE: 37

Met Gly Gly Ser His His His His His His Ser His Arg Asp Phe Gln
1               5                   10                  15

Pro Val Leu His Leu Val Ala Leu Asn Ser Pro Leu Ser Gly Gly Met
            20                  25                  30

Arg Gly Ile Arg Gly Ala Asp Phe Gln Cys Phe Gln Gln Ala Arg Ala
        35                  40                  45

Val Gly Leu Ala Gly Thr Phe Arg Ala Phe Leu Ser Ser Arg Leu Gln
    50                  55                  60

Asp Leu Tyr Ser Ile Val Arg Arg Ala Asp Arg Ala Ala Val Pro Ile
65                  70                  75                  80

Val Asn Leu Lys Asp Glu Leu Leu Phe Pro Ser Trp Glu Ala Leu Phe
                85                  90                  95

Ser Gly Glu Ser Gly Ala Gly Lys Thr Pro Gly Ala Arg Ile Phe Ser
            100                 105                 110

Phe Asp Gly Lys Asp Val Leu Arg His Pro Thr Trp Pro Gln Lys Ser
        115                 120                 125

Val Trp His Gly Ser Asp Pro Asn Gly Arg Arg Leu Thr Glu Ser Tyr
    130                 135                 140

Cys Glu Thr Trp Arg Thr Glu Ala Pro Ser Ala Thr Gly Gln Ala Ser
145                 150                 155                 160

Ser Leu Leu Gly Gly Arg Leu Leu Gly Gln Ser Ala Ala Ser Cys His
                165                 170                 175

His Ala Tyr Ile Val Leu Cys Ile Glu Asn Ser Phe Met Thr Ala Ser
            180                 185                 190

Lys

<210> SEQ ID NO 38
<211> LENGTH: 192
<212> TYPE: PRT
<213> ORGANISM: artificial sequence
<220> FEATURE:
<223> OTHER INFORMATION: mutant

```
<400> SEQUENCE: 38

Met Gly Gly Ser His His His His His Ser His Arg Asp Phe Gln
1               5                   10                  15

Pro Val Leu His Leu Val Ala Leu Asn Ser Pro Leu Ser Gly Gly Met
            20                  25                  30

Arg Gly Ile Arg Gly Ala Asp Phe Gln Cys Phe Gln Gln Ala Arg Ala
        35                  40                  45

Val Gly Leu Ala Gly Thr Phe Arg Ala Phe Leu Ser Ser Arg Leu Gln
50                  55                  60

Asp Leu Tyr Ser Ile Val Arg Arg Ala Asp Arg Ala Ala Val Pro Ile
65                  70                  75                  80

Val Asn Leu Lys Asp Glu Leu Leu Phe Pro Ser Trp Glu Ala Leu Phe
                85                  90                  95

Ser Gly Ser Glu Gly Pro Leu Lys Pro Gly Ala Arg Ile Phe Ser Phe
            100                 105                 110

Asp Gly Arg Asp Val Leu Arg His Pro Thr Trp Pro Gln Lys Ser Val
        115                 120                 125

Trp His Gly Ser Asp Pro Ser Gly His Arg Leu Thr Glu Ser Tyr Cys
130                 135                 140

Glu Thr Trp Arg Thr Asp Ser Arg Ala Ala Thr Gly Gln Ala Ser Ser
145                 150                 155                 160

Leu Leu Gly Gly Arg Leu Leu Gly Gln Ser Ala Ala Ser Cys His His
                165                 170                 175

Ala Tyr Ile Val Leu Cys Ile Ala Asn Ser Phe Met Thr Ala Ser Lys
            180                 185                 190

<210> SEQ ID NO 39
<211> LENGTH: 194
<212> TYPE: PRT
<213> ORGANISM: artificial sequence
<220> FEATURE:
<223> OTHER INFORMATION: mutant

<400> SEQUENCE: 39

Met Gly Gly Ser His His His His His Thr His Gln Asp Phe His
1               5                   10                  15

Pro Val Leu His Leu Val Ala Leu Asn Thr Pro Leu Ser Gly Gly Met
            20                  25                  30

Arg Gly Ile Arg Gly Ala Asp Phe Gln Cys Phe Gln Gln Ala Arg Ala
        35                  40                  45

Val Gly Leu Ser Gly Thr Phe Arg Ala Phe Leu Ser Ser Arg Leu Gln
50                  55                  60

Asp Leu Tyr Ser Ile Val Arg Arg Ala Asp Arg Ala Ala Val Pro Ile
65                  70                  75                  80

Val Asn Leu Lys Asp Glu Leu Leu Phe Pro Ser Trp Glu Ala Leu Phe
                85                  90                  95

Ser Gly Glu Ser Gly Ala Gly Lys Thr Gly Gly Ala Arg Ile Phe Ser
            100                 105                 110

Phe Asp Gly Arg Asp Val Leu Arg His Pro Ala Trp Pro Gln Lys Ser
        115                 120                 125

Val Trp His Gly Ser Asp Pro Ser Gly Arg Arg Leu Thr Glu Ser Tyr
130                 135                 140

Cys Glu Thr Trp Arg Thr Asp Ser Arg Ala Ala Thr Gly Gln Ala Ser
145                 150                 155                 160
```

```
Ser Leu Leu Ala Gly Arg Leu Leu Glu Gln Lys Ala Ala Gly Cys His
                165                 170                 175

Asn Ala Phe Ile Val Leu Cys Ile Glu Asn Ser Phe Met Thr Ser Ser
            180                 185                 190

Ser Lys
```

MOLECULAR DESIGN OF RECOMBINANT PROTEIN DRUG

CROSS-REFERENCE TO RELATED APPLICATIONS

This application is the national phase of PCT application PCT/CN2016/073773 having an international filing date of Feb. 14, 2016, which claims benefit of Chinese patent application Nos. 201510079486.7 filed Feb. 13, 2015, and 201510736184.2 filed Nov. 2, 2015. The contents of the above patent applications are incorporated by reference herein in their entirety.

FIELD OF THE INVENTION the present invention relates to novel recombinant protein drugs. Specifically, this invention provides variants of endostatin, when said variants have higher ATPase activity and higher activity of inhibiting angiogenesis and tumor growth compared to native endostatin. The present invention also provides the use of said variants in treating tumor and other angiogenesis-related diseases.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 783252000300SeqList.txt, date recorded: Dec. 21, 2017, size: 61,758 bytes).

BACKGROUND OF THE INVENTION

In 1997, the professor Judah Folkman of Harvard University discovered an endogenous angiogenesis inhibitor: endostatin (abbreviated as ES hereinafter). ES is an enzymatic digestion product from the carboxyl terminal of collagen XVIII, with a molecular weight of about 20 kDa, and comprises 183 amino acid residues. Recombinant endostatin can inhibit or even cure various murine tumors, without showing any drug resistance (Folkman J. et al. Cell 1997; 88:277-285; Folkman J. et al. Nature 1997; 390:404-407). The mechanism of ES in inhibiting tumor is to inhibit its angiogenesis, and to block nutrients and oxygen supply to the tumor.

Adensoine triphosphate (ATP) is the most basic energy source for life, and it is extremely important in maintaining life activities. Under normal physiological conditions, the molar concentration of ATP in cells and in blood is 1-10 mM and 100 μM respectively. ATPase, also named as adenosine triphospatase, is a class of enzymes which can catalyze the hydrolysis of ATP to release energy, and at the same time, produce adenosine diphosphate (ADP) and a phosphate ion (Pi). In addition, the high energy bond contained in guanosine triphosphate (GTP) can also provide energy for protein biosynthesis.

Many important proteins, such as Hsp90, myosin, and the like, depend on ATP for energy supply. These proteins themselves usually have ATPase activity. Although various ATPase differ in sequence and tertiary structure, they usually have an ATP-binding motif, i.e. the P-loop structure (Andrea T. Deyrup, et al., 1998, JBC, 273(16):9450-9456). A typical sequence for the P-loop structure is GXXGXXK (Driscoll, W. J., et al, 1995, Proc. Natl. Acad. Sci. U.S.A., 92:12328-12332), wherein X denotes any amino acid residue, and the other amino acid residues (two Gs and a K) are relatively more conserved. Usually, the ATP-binding motif in these ATPases can also bind GTP, so many ATPases also have GTPase activity at the same time.

When bearing a tumor, cancer cells and neovascular endothelial cells have extremely exuberant metabolic activates, and the metabolism thereof is greatly different from that in normal mature cells. On the one hand, cancer cells and exuberantly proliferating cells need to consume large amount of ATP; on the other hand, the efficiency of the cancer cells and the exuberantly proliferating cells to produce ATP from glucose is rather low, and such a low efficiency method of ATP production by aerobic glycolysis is termed the "Warburg effect". Although the efficiency of producing ATP in this method is very low, a lot of building blocks which can be used for cell structure assembly are produced during the process, which, however, is more helpful to ell proliferation (Matthew G., et al., 2009, Science, 324:1029-1033).

Prior arts show that native endostatin has very high ATPase activity, and the amino acids Gly-Ser-Glu-Gly-Pro-Leu-Lys at positions 89-95 in its sequence (SEQ ID NO:1) have the classic ATP-binding motif in the form of GXXGSSK. Prior arts show that the ATPase activity of ES if negatively related to the activity of ES to inhibit endothelial cell migration, and this phenomenon ca be explained by the Warburg Effect. This pattern has been proved and revealed in a series of ES mutants with decreased ATPase activity (PCT/CN2012/081210).

SUMMARY OF THE INVENTION

The present invention relates to the ATPase activity of ES, and ES drug designing based on such activity and ES mutants with higher anti-tumor activity are disclosed.

It is found by the present invention that, apart from the classic ATP-binding motif in the form of GXXGXXK, the native ES molecule also has another site associated with ATPase activity, i.e., an auxiliary binding motif, Val-Leu-Cys-Ile-Glu, at positions 171-175 in the native ES sequence (SEQID NO: 1), wherein said motif is in compliance with another classic form of ATP-binding motif: hhhhE (where h represents a hydrophobic amino acid residue).

It is also found the present invention that only when the two ATP-binding motifs are coordinates, can the ATPase activity of ES be ensured. Within the two motifs, the site with GXXGSSK binding motif conducts main binding and catalysis functions, and the binding motif in the form of hhhhE has an important effect on the ATPase activity by influencing the binding status of ES and substrate ATP. Thus, the ATPase activity of ES can be altered by deletion, insertion or substitution of the amino acid residues in the two ATP-binding motifs.

In the present invention, the ATP-binding motif in the ES molecule having the form of GXXGXXK is termed Walker A Motif (i.e., the A Motif). The A motif plays a major catalytic role. The ATPase activity of ES can be increased or decreased by deletion, insertion or substitution of the amino acid residues in the A Motif.

In the present invention, the ATP-binding motif in the ES molecule having the form of hhhhE is termed Walker B Motif (the B Motif). The B Motif mainly helps ES to bind ATP and does not directly catalyze the hydrolysis of ATP. Therefore, deletion, insertion or substitution of the amino acid residues in the B motif only usually reduces the ATPase activity of ES. In theory, however, for a particular A motif, appropriate changes in the B Motif can also cause increased ATPase activity. Therefore, if ES mutants with improved ATPase activity are desired, the A motif and the B motif should be adjusted adaptively in drug designing.

It is found sparingly by the present invention that for the ES mutants with significantly improved ATPase activity, their activity to inhibit endothelial cell migration and to inhibit tumor is significantly higher than that of native ES and ES mutants with decreased ATPase activity.

ES is an anti-angiogenesis protein, the most basic function of which is inhibiting angiogenesis by suppressing the activity of endothelial cells, and thus it can treat angiogenesis-related diseases, such as tumor, retinal macular degeneration, obesity, diabetes, and the like. We found that ES mutants with higher ATPase activity show improved activity in inhibiting angiogenesis-related disease (such as tumor, obesity, fatty liver, insulin resistance, and the like) than native ES or ES mutants with decreased ATPase activity.

In addition, base don the discovery of the association between the anti-angiogenesis activity of ES and its ATPase activity, ES mutants can be designed by molecular cloning approaches to further alter (e.g., increase) the ATPase activity, and therefore to obtain ES drugs which better inhibit angiogenesis-related diseases such as tumor.

The present invention also provides a method to improve the anti-tumor activity of ES or variants thereof, which includes increasing the ATPase activity of ES or variants thereof. Specifically, a mutation can be introduced into the two ATP-binding motifs of ES or variants thereof by genetic engineering approaches, so as to obtain mutants of ES or variants thereof with increased ATPase activity, wherein said mutants have improved biological activity, such as increased activity of inhibiting endothelial cell migration and increased activity of inhibiting tumor.

The present invention also provides an ES mutant which has increased anti-angiogenesis activity, wherein said mutant contains a mutation in its ATP-binding motif, and has higher ATPase activity compared to wild-type ES or some variants thereof.

Preferably, when compared to wild-type ES, the ATPase activity of said ES mutant is increased by at least 100%, meaning the ATPase activity of said ES mutant is 200% of that of the wild-type ES, 300% of that of the wild-type ES, or higher. Compared to the engineering scheme of decreasing the ATPase activity, the engineering scheme of increasing the ATPase activity has greater space for optimization.

In some embodiments, when compared to the corresponding wild-type ES or variants thereof, mutant with increased ATPase activity includes a mutation in the A motif of its ATP-binding motifs. For example, said mutant contains a mutation in the sequence corresponding to the Gly-Ser-Glu-Gly-Pro-Leu-Lys motif consisting of amino acid residues at positions 89-95 of SEQ ID NO: 1, and wherein said mutation is selected from deletion, insertion or substitution of one or several amino acids, or the combination thereof, and wherein said mutation leads to the increase of ATPase activity of said mutant.

In some embodiments, the sequence of said mutant corresponding to the A motif, i.e. the Gly-Ser-Glu-Gly-Pro-Leu-Lys motif consisting of amino acid residues at positions 89-95 of SEQ ID NO: 1, is mutated, wherein the mutation leads to the increase of ATPase activity of said mutant.

In some embodiments, said mutant contains a mutation in the B motif when compared to wild-type ES or variants thereof.

In some embodiments, the sequence of said mutant corresponding to the B motif, i.e., the Val-Leu-Cys-Ile-Glu auxiliary binding motif consisting of amino acid residues at positions 171-175 of SEQ ID NO: 1, is partially or entirely mutated.

It is also found by the present invention that, there is a C motif in ES (Walker C motif), i.e., the Glu-Ala-Pro-Ser motif consisting of amino acid residues at positions 141-144 of SEQ ID NO: 1, which has an important effect on the anti-angiogenesis activity of ES.

In some embodiments, the sequence of said mutant corresponding to the C motif, i.e. Glu-Ala-Pro-Ser motif motif consisting of amino acid residues at positions 141-144 of SEQ ID NO: 1, is partially or entirely mutated, which can increase the ATPase activity and anti-angiogenesis activity of ES.

Preferably, the Glu-Ala-Pro-Ser motif consisting of amino acid residues at positions 141-144 of SEQ ID NO: 1 which corresponds to the C motif is entirely mutated to Asp-Ser-Arg-Ala, which can increase the anti-angiogenesis function of ES.

Preferably, the mutational engineering of the motif corresponding to the C motif in the mutant can be conducted in combination with the mutational engineering of the A and B motifs, so as to further increase the anti-angiogenesis function of ES.

Preferably, applying the following engineering schemes to ES or variants thereof would increase in ATPase activity: (1) keeping the amino acid residues correspond to the conserved amino acid residues G89, G92, and K95 in the A motif GXXGXXK in SEQ ID NO: 1 unchanged; (2) increasing the spatial conformation flexibility of the peptide corresponding to the A motif by adjusting the variable resides X within the A motif GXXGXXK; (3) adding a Ser or Thr after residue K95 in the classic sequence of A motif GXXGSSK; (4) adjusting the B motif according to the change in the A motif; (5) partially or entirely mutating the amino acid residues in the C motif; (6) adjusting the C motif according to the change in the B motif; (7) adjusting the C motif according to the change in the A motif; (8) changing the A, B, and C motifs at the same time.

The 8 schemes above can be used alone respectively, and more preferably, the 8 schemes above can be used in combination to obtain better ES mutants with increased ATPase activity.

In detailed embodiments, the ES mutant of the present invention has a sequence selected from the following group: SEQ ID NO: 3-34 and SEQ ID NO: 37-39. Preferably, the endostatin mutant of the present invention has a sequence selected from the following group: SEQ ID NO: 3, SEQ ID NO: 20, SE ID NO: 21, SEQ ID NO: 24, SEQ ID NO: 25, SEQ ID NO: 26, SEQ ID NO: 28, SEQ ID NO: 29 and SEQ ID NO:30.

Preferably, the ES mutant of the present invention as described above is human ES mutant.

More preferably, the ES mutant of the present invention as described above comprises a mutation at ATPase binding site.

The present invention also provides a pharmaceutical composition, which comprises an ES mutant of the present invention as describe abode and a pharmaceutically acceptable carrier. In the pharmaceutical composition of the present invention, said ES mutant can be covalently linked to a polyethylene glycol (PEG) molecule. Preferably, said PEG molecular can be 5-40 kD, such as 5-20 kD, or 20-40 kD, preferably the molecular weight of said PEG molecule is 20 kD, such as a 20 kD monomethoxypolyethylene glycol (mPEG), such as monomethoxy polyethylene glycol propionaldehyde (mPEG-ALD) or monomethoxy polyethylene glycol butyrald (mPEG-Buty).

Preferably, the PEG molecule is covalently linked to the α-amino group at the N-terminal of said ES mutant.

The pharmaceutical composition of the present invention can be obtained by conventional methods using a pharmaceutically acceptable carrier well known in the art, for example, by formulating it into a powder or an injection.

The term "therapeutically effective amount" as used herein refers to the amount of active compound sufficient to cause the biological or medical response in human body as sought by a clinician. It will be appreciated that the dose will vary depending on the typical daily dose acceptable to a patient may range from 0.01 mg to 100 mg of active ingredient per kg of body weight.

The present invention also provides a method for treating tumor, comprising administering to a tumor patient an ES mutant of the invention or a pharmaceutical composition of the invention as described above. The administration to the subject may be conducted conveniently by a method known to those skilled in the art, such as intravenous injection.

The present invention also provides a method of treating obesity, fatty liver or insulin resistance, comprising administering to a patient suffering from obesity, fatty liver or insulin resistance an ES mutant of the invention or a pharmaceutical composition of the invention as described above.

The present invention also relates to the use of ES mutant as described above in the manufacture of a medicament for the treatment of an angiogenesis-related disease. For example, said angiogenesis-related disease may be tumor, obesity, fatty liver, insulin resistance, and the like.

BRIEF DESCRIPTION OF THE DRAWINGS

FIG. 2: purification of proteins from inclusion bodies;
(A) purification of proteins from inclusion bodies;
(B) purification of refolded proteins;
(C) purification of modified proteins;

FIG. 3: native human ES sequence, wherein the first amino acid residue M at the N-terminal can be deleted randomly when recombinantly expressed in *Escherichia coli*.

FIG. 4: the S03 sequence recombinantly expressed by *Escherichia coli*, wherein the first amino acid reside Um at the N-terminal can be deleted randomly.

FIG. 5: the S04 sequence recombinantly expressed by *Escherichia coli*, wherein the first amino acid residue M at the N-terminal can be deleted randomly.

FIG. 6: the S05 sequence recombinantly expressed by *Escherichia coli*, wherein the first amino acid residue M at the N-terminal can be deleted randomly.

FIG. 7: The S06 sequence recombinantly expressed by *Escherichia coli*, wherein the first amino acid residue M at the N-terminal can be deleted randomly.

FIG. 8: The S07 sequence recombinantly expressed by *Escherichia coli*, wherein the first amino acid residue M at the N-terminal can be deleted randomly.

FIG. 9: The S08 sequence recombinantly expressed by *Escherichia coli*, wherein the first amino acid residue M at the N-terminal can be deleted randomly.

FIG. 10: the S11 sequence recombinantly expressed by *Escherichia coli*, wherein the first amino acid residue M at the N-terminal can be deleted randomly.

FIG. 11: the S13 sequence recombinantly expressed by *Escherichia coli*, wherein the first amino acid residue M at the N-terminal can be deleted randomly.

FIG. 12: the S14 sequence recombinantly expressed by *Escherichia coli*, wherein the first amino acid residue M at the N-terminal can be deleted randomly.

FIG. 13: the S15 sequence recombinantly expressed by *Escherichia coli*, wherein the first amino acid residue M at the N-terminal can be deleted randomly.

FIG. 14: the S16 sequence recombinantly expressed by *Escherichia coli*, wherein the first amino acid residue M at the N-terminal can be deleted randomly.

FIG. 15: the S17 sequence recombinantly expressed by *Escherichia coli*, wherein the first amino acid residue M at the N-terminal can be deleted randomly.

FIG. 16: the S18 sequence recombinantly expressed by *Escherichia coli*, wherein the first amino acid residue M at the N-terminal can be deleted randomly.

FIG. 17: the S19 sequence recombinantly expressed by *Escherichia coli*, wherein the first amino acid residue M at the N-terminal can be deleted randomly.

FIG. 18: the S20 sequence recombinantly expressed by *Escherichia coli*, wherein the first amino acid residue M at the N-terminal can be deleted randomly.

FIG. 19: the NSN1 sequence recombinantly expressed by *Escherichia coli*, wherein the first amino acid residue M at the N-terminal can be deleted randomly.

FIG. 20: the NSN2 sequence recombinantly expressed by *Escherichia coli*, wherein the first amino acid residue M at the N-terminal can be deleted randomly.

FIG. 21: the NSN3 sequence recombinantly expressed by *Escherichia coli*, wherein the first amino acid residue M at the N-terminal can be deleted randomly.

FIG. 22: the NSN4 sequence recombinantly expressed by *Escherichia coli*, wherein the first amino acid residue M at the N-terminal can be deleted randomly.

FIG. 23: the E176A sequence recombinantly expressed by *Escherichia coli*, wherein the first amino acid residue M at the N-terminal can be deleted randomly.

FIG. 24: the C174E sequence recombinantly expressed by *Escherichia coli*, wherein the first amino acid residue M at the N-terminal can be deleted randomly.

FIG. 25: the E-M sequence recombinantly expressed by *Escherichia coli*, wherein the first amino acid residue M at the N-terminal can be deleted randomly.

FIG. 26: comparison of unmodified ES mutants S03, NSN4 and E-M on the activity of inhibiting migration of endothelial cells.

FIG. 33: the sequences of ES mutants 36 (SEQ ID NO: 25), 249 (SEQ ID NO: 26), 381 (SEQ ID NO: 27), 57 (SEQ OD NO: 28), 114 (SEQ ID NO: 29), 124 (SEQ ID NO; 30) and 125 (SEQ ID NO: 31).

FIG. 34: the sequences of ES mutants 160 (SEQ ID NO: 32) (SEQ ID NO: 33) and 119 (SEQ ID NO: 34).

FIG. 35: comparison of unmodified ES mutants 36, 249, 381 and modified ES mutants M36, M249, M381 on the activity of inhibiting migration of endothelial cells.

FIG. 36: comparison of modified ES mutants NSN4, M249, M119, M160, M163, M125, M57, M124 and M114 on the activity of inhibiting migration of endothelial cells.

FIG. 37: the sequences of unmodified ES mutants Endu-D-M (SEQ ID NO: 37), Endu-114 (SEQ ID NO: 38) and Endu-57 (SEQ ID NO: 39).

DETAILED DESCRIPTION OF THE INVENTION

Figure 1:
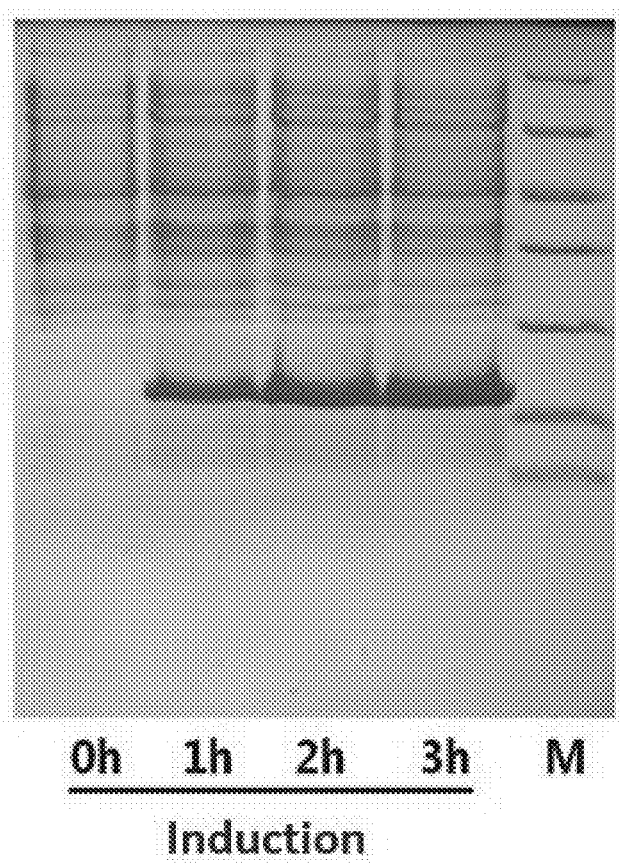
FIG. 1: expression of ES mutant S03 in engineered bacteria.

Unless otherwise indicated, the scientific and technical terms used in this specification should have the meanings that are commonly understood by a skilled person in the art. In general, the names and techniques associated with cellular and tissue culture, molecular biology, immunology, microbiology, genetics and protein and nucleic acid chemistry used in the present specification are well known and commonly used in the art.

Unless otherwise indicated, the methods and techniques used in this specification are generally carried out according to the conventional methods or references cited in this specification.

ES, ES Mutants and PEG Modified Products

ES (Endostatin) refers to native endostatin, such as human endostatin having the sequence of SEQ IS NO: 1, and when the human ES is recumbently expressed in *E. coli*, an amino acid residue M will be randomly added to N-terminal of some products (FIG. 3). In the present application, an ES mutant refers to a mutant protein obtained by mutating one or some amino acid residues of an ES variant, such as amino acid deletion, insertion or substitution in an ATP-binding motif. ES mutants can be naturally occurring, for example, when ES is recombinantly expressed in yeast, an ES mutant with an N-terminal deletion of 4 amino acids can be produced due to random deletion at the N-terminal, and furthermore, the C-terminal K can also be randomly deleted. ES mutants can also be artificially constructed, for example, in order to promote protein expression and improve stability, Endu is a mutant produced by adding nine additional amino acid residues MGGSHHHHH to the N-terminal of native ES by genetic engineering means, wherein the first amino acid M can be randomly deleted when recombinant expressed in *E. coli*, which makes Endu have the sequence of SEQ ID NO: 2.

The unmodified and modified ES and ES mutant proteins in the present invention were all provided by Beijing Protgen Ltd.

Polyethylene glycol (PEG)-modified ES is named M2ES, and PEG-modified ES mutants are named by adding "M" prior to the mutant designation: for example, PEG-modified ES mutant S03 is named MS03 and PEG-modified ES mutant NSN1 is named MNSN1. For example, in some detailed embodiments of the present invention, the molecule named MS03 or MNSN1 may be the product of a mutant called S03 or NSN1 modified by monomethoxypolyethylene glycol propionaldehyde (mPEG-ALD) with a molecular weight of 20 kD, and the coupling sites are the activated mPEG-ALD aldehyde group and the N-terminal α-amino group of S03 or NSN1.

ATP-binding motif refers to a typical amino acid sequence that binds to ATP in a protein molecule with ATPase activity. The ATP-binding motif usually has a P-loop structure, and the P-loop structure has the following typical sequences GXXGXXK, (G/A)XXXXGK(T/S), GXXXXGKS and GXXGXGKS. For human ES, the ATP-binding motif mainly refers to the sequence in a form of GXXGXXK, wherein the amino acid residues which are not substituted by X are more conserved. In general, these ATP-binding motifs can also bind to GTP, UTP, CTP, and the like.

The ATP-binding motifs referred to in the present invention include the A motif (Walker A motif), the B motif (Walker B motif) and the C motif (Walker C motif). The A motif refers to the site with a sequence in the form of GXXGXXK, wherein X is a variable amino acid residue. The A motif is the main site for ES and ATP-binding and catalytic hydrolysis. The B motif refers to the site with sequence in the form of hhhhE, wherein h is a hydrophobic amino acid residue. The B motif is involved in the binding of ATP to ES and affects the ATPase activity of ES by influencing the binding of ES to ATP. The C motif refers to the site with a senesce of Glu-Ala-Pro-Ser (i.e. EAPS) in the ES molecule and is likely to affect the ATPase activity of ES by indirectly influencing the binding of ES and ATP, which needs to be verified by the information of the crystal structure of ES-ATP complex. In addition, since the spatial conformation of a protein is formed by the folding of the peptide chain, the adjacent amino acid residues in the primary sequence are often not close to each other in the spatial conformation; conversely, the amino acid residues far apart in the primary sequence are close to each other in the spatial conformation. The stability of the local conformation of protein molecules is largely dependent on the stability of the overall molecular conformation, and the change of local amino acid sequence may lead to the change of overall molecular conformation. Thus, it will be appreciated by those skilled in the art that there are other sites involved in the regulation of ES and ATP interaction apart from the three motifs of A, B, and C, which can also affect the ATPase activity of ES and inhibit angiogenesis. These sites may play a role alone or in combination with the A, B, C motifs or any combination thereof to influence the ATPase activity of ES and inhibit angiogenesis. Thus in some embodiments of the present invention, in addition to mutations in the A, B, C motifs or combinations thereof, mutations have been introduced to sites other than the three motifs to achieve better results.

We have found that the ATPase activities of the tested ES, ES variants, ES mutants and their mPEG modified products are positively related to the activity of inhibiting endothelial cell migration, that is, the ES mutants with high activity of inhibiting endothelial cell migration also have high ATPase activity. Based on this finding, in order to obtain ES with high activity of inhibiting endothelial cell migration, we can increase the ATPase activity of ES by amino acid deletion, insertion or substitution in the ATP-binding motifs of ES.

Accordingly, the present invention also provides a method of increasing the activity of ES or its variants of inhibiting angiogenesis and tumor growth, including increasing the ATPase activity of ES or its variants. Specifically, by genetic engineering means, mutations can be introduced to ES or variants thereof in the A motif GXXGXXK which participates in ATP-binding, or in the A motif and the B motif simultaneously, or in the C motif, or in any combination of A, B and C motifs to obtain mutants of ES or variants thereof with increased ATPase activity. These mutants have improved biological activities, such as increased activity of inhibiting angiogenesis (such as inhibiting migration of endothelial cells) and increased activity of inhibiting tumor growth. Among them, mutations in the B motif usually lead to decreased activity of inhibiting angiogenesis and tumor growth, so particular attention should be paid to the mutations in the B motif.

Thus, in an example of the present invention, the following mutations were introduced to the A motif or the B motif of ES:

S03—SEQ ID NO: 3 (FIG. 4)
S04—SEQ ID NO: 4 (FIG. 5)
S05—SEQ ID NO: 5 (FIG. 6)
S06—SEQ ID NO: 6 (FIG. 7)
S07—SEQ ID NO: 7 (FIG. 8)
S08—SEQ ID NO: 8 (FIG. 9)
S11—SEQ ID NO: 9 (FIG. 10)
S13—SEQ ID NO: 10 (FIG. 11)
S14—SEQ ID NO: 11 (FIG. 12)
S15—SEQ ID NO: 12 (FIG. 13)
S16—SEQ ID NO: 13 (FIG. 14)
S17—SEQ ID NO: 14 (FIG. 15)
S18—SEQ ID NO: 15 (FIG. 16)
S19—SEQ ID NO: 16 (FIG. 17)
S20—SEQ ID NO: 17 (FIG. 18)
NSN1—SEQ ID NO: 18 (FIG. 19)
NSN2—SEQ ID NO: 19 (FIG. 20)
NSN3—SEQ ID NO: 20 (FIG. 21)
NSN4—SEQ ID NO: 21 (FIG. 22)
E176A—SEQ ID NO: 22 (FIG. 23)
C174E—SEQ ID NO: 23 (FIG. 24)
E-M—SEQ ID NO: 24 (FIG. 25)
36—SEQ ID NO: 25 (FIG. 33)
249—SEQ ID NO: 26 (FIG. 33)
381—SEQ ID NO: 27 (FIG. 33)
57—SEQ ID NO: 28 (FIG. 33)
114—SEQ ID NO: 29 (FIG. 33)
124—SEQ ID NO: 317 (FIG. 33)
125—SEQ ID NO: 31 (FIG. 33)
160—SEQ ID NO: 32 (FIG. 34)
163—SEQ ID NO: 33 (FIG. 34)
119—SEQ ID NO: 34 (FIG. 34)
Endu-E-M—SEQ ID NO: 37 (FIG. 37)
Endu-57—SEQ ID NO: 38 (FIG. 37)
Endu-114—SEQ ID NO: 39 (FIG. 37)

When ATPase activity was measured by biochemical methods, it was found that ATPase activity of mutants with increased activity of inhibiting endothelial cell migration was significantly higher than that of ES (Table 1).

It was found that the changes in ATPase activity and the activity of inhibiting endothelial cell migration of Endu caused by mutations in ATP-binding motifs were similar to those changes in the ES related activities cause by the same mutations. Therefore, we believe that the method of altering the ATPase activity and the activity of inhibiting endothelial cell migration by mutating ATP-binding motifs in ES is also applicable to ES mutants.

Thus, the present invention also provides ES mutants having an increased activity of inhibiting angiogenesis, wherein the mutants comprise a mutation in their A motif and/or B motif and/or C motif, and the ATPase activity of the mutants is increased compared to the corresponding wild-type ES or variants thereof.

Preferably, the ATPase activity of the ES mutants is increased by at least 100% compared to the wild-type ES, i.e., the ATPase activity of the mutants is 200% of that of the wild-type ES, 300% or more of that of the wild-type ES.

In some embodiments, the mutants comprise mutations in their ATP-binding motifs compared to the corresponding wild-type ES or ES variants. For example, the mutants have mutations in the sequence corresponding to the Gly-Ser-Glu-Gly-Pro-Leu-Lys motif consisting of amino acid residues at positions 89-95 of SEQ ID NO: 1, wherein the mutations are selected from substitution, deletion or addition of one or several amino acid residues, or a combination thereof, which makes the mutants have increased ATPase activity.

Preferably, applying the following engineering schemes to ES or variants thereof would increase in ATPase activity: (1) keeping those corresponding to the conserved amino acid residues G89, G92, and K95 in the A motif GXXGXXK of SEQ ID NO: 1 unchanged; (2) increasing the spatial conformation flexibility of the peptide corresponding to the A motif by adjusting the variable residue X within the A motif GXXGXXK; (3) optionally adding a Ser or thru after residue K95 in the sequence of classic A motif GXXGXXK; (4) adjusting the B motif according to the change in the A motif; (5) partially or entirely mutating the amino acid residues in the C motif; (6) adjusting the C motif according to the change in the B motif; (7) adjusting the C motif according to the change in the A motif; (8) changing the A, B, and C motifs at the same time.

In detailed embodiments, the ES mutant of the present invention comprises a sequence selected from the following group consisting of: SEQ ID NO: 3-21, and 24. Preferably, the endostatin mutant of the present invention comprises a sequence selected from the following group consisting of: SEQ ID NO: 3, SEQ ID NO: 20, SEQ ID NO: 21, and SEQ ID NO: 24.

Preferably, the ES mutant of the present invention is human ES mutant.

The present invention also provides a method of treating tumor, comprising administering to the patient an effective amount of an endostatin mutant of the present invention as described above or a pharmaceutical composition of the present invention as described above. The angiogenesis-related diseases include tumor, obesity, fatty liver and insulin resistance. Preferably, the angiogenesis-related disease is tumor.

The present invention is further illustrated by the following on-limiting examples. It is to be understood that the invention is not limited to these examples.

EXAMPLES

Example 1: Construction of ES Recombinant Strains

Figures 30, 31, 32:
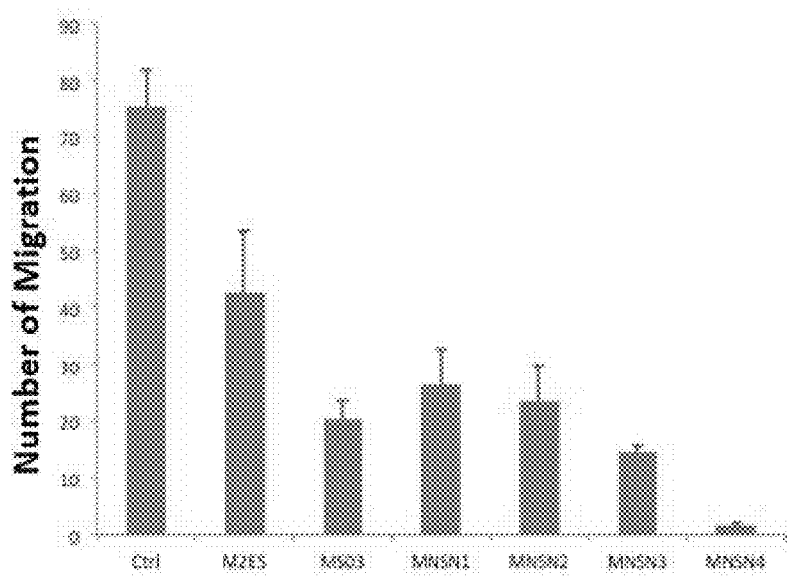
FIG. 30: comparison of modified ES mutants MS03, MSN1, MNSN2, MNSN3 and MNSN4 on the activity of inhibiting migration of endothelial cells.
FIG. 31: forward PCR primer sequence for amplification of ES. (SEQ ID NO: 35)
FIG. 32: reverse PCR primer sequence for amplification of ES. (SEQ ID NO; 36)

In this example, Endostatin was cloned from the cDNA of human lung caner cell A549, and ligated into pET30a plasmid. The 5' primer used for gene amplification was GGAATTCCATATGCACAGCCACCGCGACTTC (FIG. 31, SEQ ID NO:35) and the 3' primer was CCGCTCGAGTTACTTGGAGGCAGTCATGAAGCTG (FIG. 32, SEQ ID NO: 36). Endonucleases were NdeI and XhoI, respectively.

The recombinant plasmids described above were transformed into *E. coli* according to conventional molecular cloning techniques and expressed.

Example 2: Construction of ES Mutant Strains with ATP-Binding Motif Mutations

In this example the ATP-binding motif of wild-type human ES was subjected to mutational engineering. The upstream and downstream primers and the transformation method were the same as those in Example 1. The mutants' numbers and the changes occurred are as follows:

S03—SEQ ID NO: 3 (FIG. 4) four amino acid residues HSHR at the N-terminal were deleted, while the A motif was mutated to be GESGAGK, and T was inserted;

S04—SEQ ID NO: 4 (FIG. 5) four amino acid residues HSHR at the N-terminal were deleted, S was inserted after the A motif. At the same time, the E and subsequent amino acid residues NSFMTASK in the B motif were deleted;

S05—SEQ ID NO: 5 (FIG. 6) four amino acid residues HSHR at the N-terminal were deleted, T was inserted after the A motif. At the same time, the E and subsequent amino acid residues NSFMTASK in the B motif were deleted;

S06—SEQ ID NO: 36(FIG. 4) four amino acid residues HSHR at the N-terminal were deleted, while the A motif was mutated to be GESGAGK and then T was inserted. At the same time, the E and subsequent amino acid residues NSFMTASK in the B motif were deleted;

S07—SEQ ID NO: 7 (FIG. 8) four amino acid residues GESGAGK and T was inserted. At the same time, deleted the C-terminal amino acid residues SFMTASK;

S08—SEQ ID NO: 8 (FIG. 9) the A motif was mutated to be GESGAGK and T was inserted. At the same time, the C-terminal amino acid residues TASK were deleted;

S11—SEQ ID NO: 9 (FIG. 10) the C-terminal amino acid residues SFMTASK were deleted;

S13—SEQ ID NO: 10 (FIG. 11) the N-terminal residues HS were deleted, the A motif was mutated to be GESGAGK and T was inserted. At the same time, the C-terminal SFMTASK were deleted;

S14—SEQ ID NO: 11 (FIG. 12) the N-terminal resides HS were deleted, the A motif was mutated to be GESGAGK and T was inserted. At the same time, the C-terminal TASK were deleted;

S15—SEQ ID NO: 12 (FIG. 13) the N-terminal residues HS were deleted, the A motif was mutated to be GESGAGK and T was inserted. At the same time, the C-terminal K was deleted;

S16—SEQ ID NO: 13 (FIG. 14) the N-terminal reissue H was deleted, the A motif was mutated to be GESGAGK and T was inserted. At the same time, the C-terminal K was deleted;

S17—SEQ ID NO: 14 (FIG. 15) the N-terminal residue H was deleted, the A motif was mutated to be GESGAGK and T was inserted. At the same time, the C-terminal SFMTASK were deleted;

S18—SEQ ID NO: 15(FIG. 16) the N-terminal residue H was deleted, the A motif was mutated to be GESGAGK and T was inserted. At the same time, the C-terminal TASK were deleted;

S19—SEQ ID NO: 16 FIG. 17) the N-terminal residue H was deleted, the A motif was mutated to be GESGAGK and T was inserted;

S20—SEQ ID NO: 17 (FIG. 18) the N-terminal residues HS were deleted, the A motif was mutated to be GESGAGK and T was inserted;

NSN1—SEQ ID NO: 18 (FIG. 19) deleted Ser-88, the A motif was mutated to be GESGAGK and T was inserted;

NSN2—SEQ ID NO: 19 (FIG. 20) the A motif was mutated to be GESGAGK, P96T&G97P;

NSN3—SEQ ID NO: 20 (FIG. 21) the A motif was mutated to be GESGAGK, P96T;

NSN4—SEQ ID NO: 21 (FIG. 22) the A motif was mutated to be GESGAGK, P96T; Gly-98 was inserted;

E176A—SEQ ID NO: 22 (FIG. 23) E176A;

C174E—SEQ ID NO: 23 (FIG. 24) C174E;

E-M—SEQ ID NO: 24 (FIG. 25) the A motif was mutated to be GESGAGK, and T was inserted.

Example 3: Expression and Preparation of Recombinant ES and its Mutants

In this example, the expression and preparation methods of ES and its mutants are briefly described as follows taking S03 as an example: ES or its mutant engineering strains were spreading cultivated overnight in LB medium shaking flask, inoculated into a 5 L fermentor (Sartorius), and IPTG was added timely for induction. After induction, cultivation was continued for about 4 hours, then the bacterial were collected, and analyzed by electrophoresis (FIG. 1).

The bacteria cells were resuspended in PBS buffer and were thoroughly crushed with a high-pressure homogenizer, repeatedly for three times, and each time after crushing were centrifuged to collect the sediment, which was then resuspended in PBS buffer. The sediment of crushed bacteria was dissolve din Tris-HCl buffer containing 8 M urea (PH 8.5) and then eluted with DEAE chromatography media (GE Healthcare) with Tris-HCl buffer at pH 8.5. The penetrated fraction was collected and a purified protein before renaturation was obtained. After refolding the protein, gradient elution was performed using a CM chromatography media (GE Healthcare) with Tris-HCl buffer at pH 8.5 with a salt concentration ranged from 0 to 500 mM NaCl to obtain a refolded protein with a purity greater than 95% (FIG. 2A, B). The refolded protein was dialyzed against NaAc-HAc (pH 6.0). Monomethoxypolyethylene glycol propanal (mPEG-ALD, 20 kDa, Beijing JianKai Technology Co., Ltd) with an average molecular weight of 20 kD was used to perform N-terminal single modification of the refolded protein according to the operation method of described in the product specification. The modified product was purified using a SP column (GE Healthcare), gradient elusion was performed using NaCl with a concentration of 0-500 mM to give the target fractions (FIG. 2C).

The preparation of other ES mutants and their modified products were the same as described above.

Example 4: Assay for ATPase Activity of ES, ES Mutants and their mPEG Modified Products A method for testing ATPase activity disclosed in prior art (PCT/CN2012/081210) was used in this example. The ATPase activity of ES, ES mutants and their mPEG modified products was tested. The results were shown in Table 1, Protein Myosin (extracted from pig heart, Sigma) with relatively high ATPase activity was used as a positive control in this assay.

Example 5: Activity of ES and ES Mutants to Inhibit Endothelial Cell Migration

The Transwell endothelial cell assay disclosed in prior art (PCT/CN2012/081210) was used in this example. The endothelial cells HMEC were divided into the following groups and were treated differently. The first group: negative control group, no ES (the same amount of buffer solution was added) treatment; the second group: ES (20 µg/mL) treatment; the third group: ES mutant YH-16 (20 µg/mL) treatment; the fourth group: ES mutant S03 (20 µg/mL) treatment; the fifth group: ES mutant NSN4 (20 µg/mL) treatment; the sixth group: ES mutant E-M (20 µg/mL) treatment. The results showed that the activity of S03, NSN4 and E-M to inhibit the endothelial cell migration was significantly increased compared to ES. The number of migrated cells of the S03, NSN4 and E-M treatment groups were approximately 30%, 16% and 40% of the ES treatment group, respectively (FIG. 26).

Figure 27:
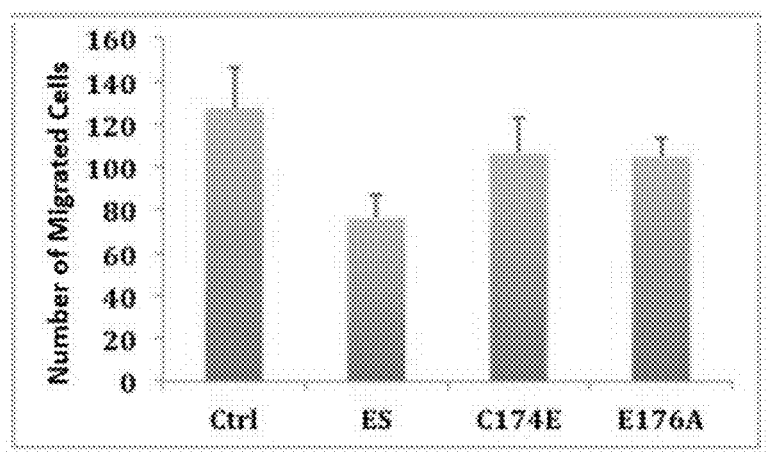
FIG. 27: comparison of ES mutants E176A and C174E on the activity of inhibiting migration of endothelial cells.
Figure 28:
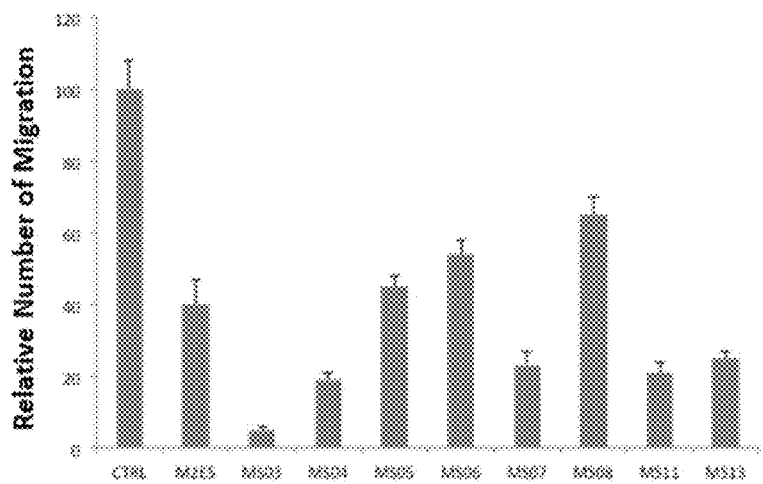
FIG. 28: comparison of modified ES mutants MS03, MS04, MS05, MS06, MS07, MS08, MS11, and MS13 on the activity of inhibiting migration of endothelial cells.
Figure 29:
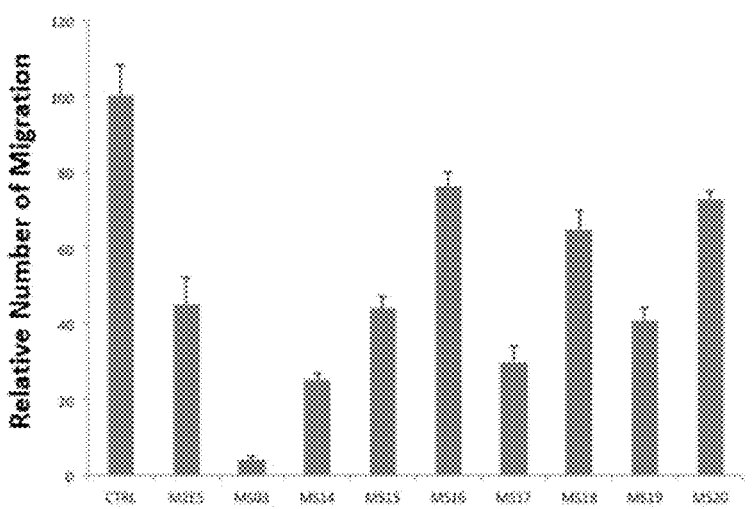
FIG. 29: comparison of modified ES mutants MS03, MS14, MS15, MS16, MS17, MS18, MS19, and MS20 on the activity of inhibiting migration of endothelial cells.

The activity of ES mutants E176A and C174E to inhibit endothelial cell migration were tested using the same assay. The activity of E 176A and C174E to inhibit endothelial cell migration were both lower than ES (FIG. 27).

Figure 38:
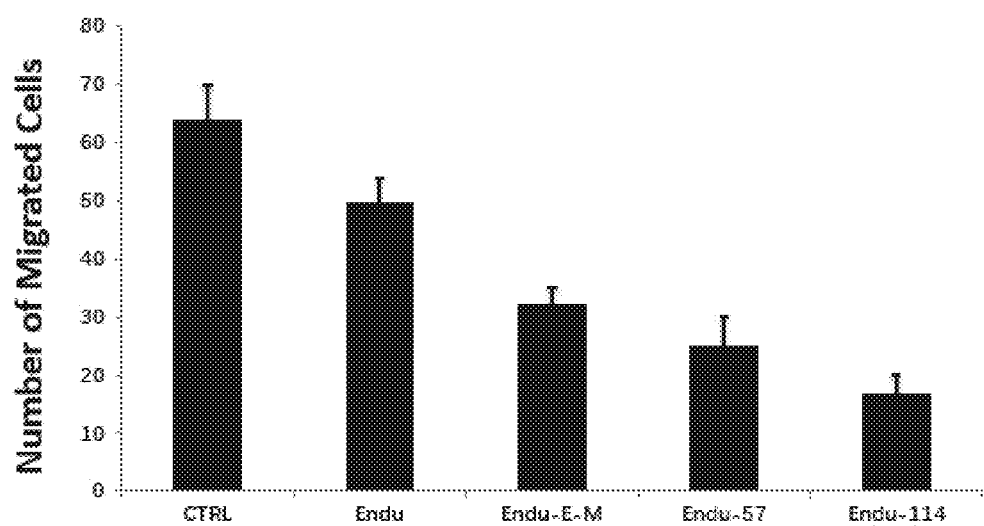
FIG. 38: comparison of unmodified ES mutants Endu-E-M, Endu-114 and Endu-57 on the activity of inhibiting migration of endothelial cells.

Example 6: Activity of mPEG-modified ES, ES Mutants to Inhibit Endothelial Cell Migration The activity of mPEG-modified ES, ES mutants to inhibit endothelial cell migration was tested by the method described in Example 5. Since the increase of the activity of inhibiting endothelial cell migration was significant for many mutant proteins, and in order to reflect the difference in activity between the mutant proteins more clearly, in this example a reduced dose (i.e. 5 μg/mL) was used to treat the cells, and obvious inhibition effect was still able to be observed, as follows:

the activity of mPEG-modified ES mutants MS03, MS04, MS05, MS06, MS07, MS08, MS11, MS13 to inhibit endothelial cell migration (FIG. 28). Among them, the activity of MS03, MS04, MS07, MS11, MS13 to inhibit endothelial cell migration was significantly better than that of M2ES: the number of migrated cells of the MS03 treatment group was about ⅛ of that of the M2ES treatment group, the number of migrated cells of the MS04, MS07, MS11 and MS13 treatment group was about ½ of that of the M2ES treatment group; while the activity of MS05, MS06 and MS08 to inhibit endothelial cell migration was lower than that of M2ES.

The activity of mEG-modified ES mutants MS03, MS14, MS15, MS16, MS17, MS18, MD19, MS20 to inhibit endothelial cell migration (FIG. 29). Among them, the activity of MS03, MS14, MS17 to inhibit endothelial cell migration was significantly better than that of M2ES; the activity of MS15, MS19 to inhibit endothelial cell migration had no significant difference with that of M2ES; the activity of MS16, MS20 to inhibit endothelial cell migration was lower than that of M2ES.

The activity of mPEG-modified ES mutants MS03, MNSN1, MNSN2, MNSN3, MNSN4 to inhibit endothelial cell migration (FIG. 30). The activity of MS03, MNSN1, MNSN2, MNSN3 and MNSN4 to inhibit endothelial cell migration was significantly better than that of M2ES, and wherein the number of migrated cells of the MNSN4 treated group was about ½ of that of M2ES.

Mutations were increased ATPase activity showed comparable of significantly increased activity of inhibiting endothelial cell migration to that of ES, which is consistent with the positive correlation between the activity of ATPase and the activity of inhibiting endothelial cells migration.

Example 7: Construction of ES Mutant Strains

In this example, mutant engineering was made on wild-type human ES, specific methods, upstream and downstream primers and engineering methods were the same as in Example 1. The mutants' numbers and their sequences are shown in FIG. 33 and FIG. 34.

36—SEQ ID NO: 25 (FIG. 33) 3 amino acid residues HSH at the N-terminal were deleted, A39Q, and Gly-89 was deleted;

249—SEQ ID NO: 26 (FIG. 33) 3 amino acid residues HSH at the N-terminal were deleted, the A motif was mutated to GSQGQLQ, the C motif was mutated to be DERG.

381—SEQ ID NO: 27 (FIG. 33) the A motif was mutated to be GSEAPLR;

57—SEQ ID NO: 28 (FIG. 33) the A motif was mutated to be GESGAGK, the C motif was mutated to be DSRA;

114—SEQ ID NO: 29 (FIG. 33) the B motif was mutated to be VLCIA, the C motif was mutated to be DSRA;

124—SEQ ID NO: 30 (FIG. 33) 4 amino acid residues HSHR at the N-terminal were mutated, the A motif was mutated to be GSEGPLR, the C motif was mutated to be DSRA;

125—SEQ ID NO: 31 (FIG. 33) 4 amino acid residues at the N-terminal were mutated, the A motif was mutated to be GSEGPLR, the C motif was mutated to be DSRA, and K was added at the C-terminal;

150—SEQ ID NO: 32 (FIG. 34) amino acid residues other than the A, b, and C motifs were mutated, see the sequence.

163—SEQ ID NO: 3 (FIG. 34) the A motif was mutated to be GSQGOLQ, the C motif was mutated to be ETTG;

119—SEQ ID NO: 34 (FIG. 34) the A motif was mutated to be VSQGQLQ.

Example 8: Activity of mPEG-modified ES and ES Mutants to Inhibit Endothelial Cell Migration The activity of mPEG-modified ES and ES mutants to inhibit endothelial cell Migration The activity of mPEG-modified ES and ES mutants to inhibit endothelial cell migration was tested by the method describe din Example 6, detailed as follows:

The activity of mPEG-modified ES mutants 36, 249, 381 and modified ES mutants M36, M249, M381 to inhibit endothelial cell migration (FIG. 35). Among them, the number of migrated cells in the 36 treatment group was about 70% of that in the ES treatment group. There was no significant difference between the activity of the 249 and 381 group and the activity of the ES group in inhibiting endothelial cells migration; the number of migrated cells in the modified mutant M36 treatment group was about 50% of that in the ES treatment group; There was no significant difference between activity of the M249, M381 group and the activity of ES group in inhibiting endothelial cells migration.

The activity of mPEG-modified ES mutants NSN4, M249, M119, M160, M163, M125, M57, M124, M114 to inhibit endothelial cell migration (FIG. 36). The activity of NSN4, M249, M160, M163, M125, M57, M124, M114, to inhibit endothelial cell migration was significantly increased compared to that of M2ES. M119 has not significant difference compared to M3ES. Among them, the number of migrated cells in the M57, M124 and M114 treated groups was about 34%, 28% and 24% of that in the M2ES treated group respectively.

Example 9: Construction of ES Mutant Strains

In this example, mutational engineering was made on Endu, and the specific methods, upstream and downstream primers and transformation methods were the same as those in Example 1. The mutants' numbers and their sequences are shown in FIG. 37.

Endu-E-M—SEQ ID NO: 37 (FIG. 37) MGGSHHHHH was added at the N-terminal, the A motif was mutated to GESGAGK, and T was inserted thereafter;

Endu-57—SEQ ID NO: 38 (FIG. 37) MGGHHHHH was added at the N-terminal, the A motif was mutated to GESGAGK, and T was inserted thereafter;

Endu-114—SEQ ID NO: 39 (FIG. 37) MGGSHHHHH was added at the N-terminal, the A motif was mutated to GEGSGAGK, and T was inserted thereafter;

Example 10: The Activity of Inhibiting Endothelial Cell Migration of mPEG-modified ES mutants The activity of inhibiting endothelial cell migration of mPEG-modified ES mutants Endu-E-M, Endu-57, Endu-114 was tested by the method described in Example 6 (FIG. 38).

The activity of inhibiting endothelial cell migration of Endu-E-M, Endu-57 and Endu-114 was significantly better than that of Endu (control), and the inhibition rates were 64%, 50% and 34% respectively.

TABLE 1

| Sample Number | Sample name | ATPase activity (nM/mg/min) | Sample name | ATPase activity (nM/mg/min) |
|---|---|---|---|---|
| 1 | ES | 14920 | mPEG-ES | 2596 |
| 2 | Endu | 5586 | mPEG-Endu | 1626 |
| 3 | S03 | 26110 | MS03 | 4585 |
| 4 | S04 | 24021 | MS04 | 4057 |
| 5 | S05 | 22828 | MS05 | 4269 |
| 6 | S06 | 19693 | MS06 | 3474 |
| 7 | S07 | 23128 | MS07 | 3987 |
| 8 | S08 | 19995 | MS08 | 3571 |
| 9 | S11 | 24322 | MS11 | 4286 |
| 10 | S13 | 24737 | MS13 | 4275 |
| 11 | S14 | 23250 | MS14 | 4051 |
| 12 | S15 | 20679 | MS15 | 3520 |
| 13 | S16 | 21082 | MS16 | 3780 |
| 14 | S17 | 22866 | MS17 | 4011 |
| 15 | S18 | 21421 | MS18 | 3716 |
| 16 | S19 | 22160 | MS19 | 3874 |
| 17 | S20 | 21025 | MS20 | 3652 |
| 18 | NSN1 | 23754 | MNSN1 | 4131 |
| 19 | NSN2 | 23345 | MNSN2 | 4136 |
| 20 | NSN3 | 26605 | MNSN3 | 4869 |
| 21 | NSN4 | 31809 | MNSN4 | 5807 |
| 22 | E176A | 5626 | ME176A | 1012 |
| 23 | C174E | 7809 | MC174E | 1405 |
| 24 | E-M | 19396 | ME-M | 3463 |

The invention claimed is:

1. A method for increasing the anti-angiogenesis activity of an endostatin or variant thereof, comprising genetically engineering the A motif of the endostatin or variant thereof, to obtain an endostatin mutant with increased ATPase activity compared to the endostatin or variant thereof, wherein said endostatin mutant comprises the sequence set forth in SEQ ID NO: 3.

2. The method of claim 1, further comprising covalently linking said mutant to a PEG molecule.

3. The method of claim 2, wherein said PEG molecule has a molecular weight of 5-40 kD.

4. The method of claim 2, wherein said PEG molecule is covalently linked to the α-amino group at the N-terminal of said mutant.

5. The method of claim 2, wherein said PEG molecule is monomethoxypolyethylene glycol.

6. The method of claim 2, wherein said PEG molecule is monomethoxypolyethylene glycol propionaldehyde (mPEG-ALD).

7. The method of claim 1, further comprising administering said mutant to a subject in need thereof for inhibiting endothelial cell migration in the subject.

* * * * *